US012576048B2

(12) United States Patent
Sharabi

(10) Patent No.: US 12,576,048 B2
(45) Date of Patent: Mar. 17, 2026

(54) ANTI-CANCER ACTIVITY OF ADAMANTANE DERIVATIVES

(71) Applicant: The Regents of the University of California, Oakland, CA (US)

(72) Inventor: Andrew Sharabi, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1237 days.

(21) Appl. No.: 17/311,101

(22) PCT Filed: Dec. 5, 2019

(86) PCT No.: PCT/US2019/064760
§ 371 (c)(1),
(2) Date: Jun. 4, 2021

(87) PCT Pub. No.: WO2020/118096
PCT Pub. Date: Jun. 11, 2020

(65) Prior Publication Data

US 2021/0330605 A1 Oct. 28, 2021

Related U.S. Application Data

(60) Provisional application No. 62/775,731, filed on Dec. 5, 2018.

(51) Int. Cl.

| | |
|---|---|
| ***A61K 31/13*** | (2006.01) |
| ***A61K 31/16*** | (2006.01) |
| ***A61K 45/06*** | (2006.01) |
| ***A61K 47/60*** | (2017.01) |
| ***A61P 35/00*** | (2006.01) |

(52) U.S. Cl.
CPC .............. *A61K 31/13* (2013.01); *A61K 31/16* (2013.01); *A61K 45/06* (2013.01); *A61P 35/00* (2018.01); *A61K 47/60* (2017.08)

(58) Field of Classification Search
CPC ........ A61K 31/13; A61K 31/16; A61K 45/06; A61K 47/60; A61P 35/00; A61P 35/02; A61P 35/04
See application file for complete search history.

(56) References Cited

U.S. PATENT DOCUMENTS

| | | | |
|---|---|---|---|
| 5,061,703 | A | 10/1991 | Bormann et al. |
| 2011/0190291 | A1 | 8/2011 | Renslo et al. |
| 2011/0218241 | A1 | 9/2011 | Preston et al. |
| 2011/0293705 | A1 | 12/2011 | Irvine et al. |
| 2013/0072553 | A1 | 3/2013 | Xu |
| 2015/0290160 | A1 | 10/2015 | Cheng et al. |
| 2018/0215699 | A1 | 8/2018 | Humbert et al. |
| 2020/0399348 | A1 | 12/2020 | Wieland et al. |

FOREIGN PATENT DOCUMENTS

| | | |
|---|---|---|
| CN | 102070463 | 5/2011 |
| WO | WO 2014075187 | 5/2014 |
| WO | WO 2019/164970 A1 | 8/2019 |

OTHER PUBLICATIONS

Um, S. H. et al. Variable expression of the forgotten oncogene E5 in HPV-positive oropharyngeal cancer. J Clin Virol., 2014. vol. 61(1): 94-100. (Year: 2014).*
Rzeski et al., "Glutamate antagonists limit tumor growth," Proceedings of the National Academy of Sciences, May 22, 2001, 98(11):6372-6377.
Wetherill et al., "Alkyl-imino sugars inhibit the pro-oncogenic ion channel function of human papillomavirus (HPV) E5," Antiviral Research, Oct. 1, 2018, 158:113-121.
Wetherill et al., "High-risk human papillomavirus E5 oncoprotein displays channel-forming activity sensitive to small-molecule inhibitors," Journal of Virology, May 1, 2012, 86(9):5341-5351.
Cohen et al., "Pembrolizumab versus methotrexate, docetaxel, or cetuximab for recurrent or metastatic head-and-neck squamous cell carcinoma (Keynote-040): a randomised, open-label, phase 3 study," Lancet, Jan. 2019, 393:156-167.
Conway et al., "Replication and Assembly of Human Papillomaviruses," Journal of Dental Research, Apr. 2009, 88(4):307-317.
Extended European Search Report in European Appln No. 19892331.0, dated Jan. 20, 2022, 10 pages.
Ferris et al., "Nivolumab for Recurrent Squamous-Cell Carcinoma of the Head and Neck," The New England Journal of Medicine, Nov. 2016, 375(19):1856-1867.
Hoppe-Seyler et al., "The HPV E6/E7 Oncogenes: Key Factors for Viral Carcinogenesis and Therapeutic Targets," Trends in Microbiology, Feb. 2018, 26(2):158-168.
International Preliminary Report on Patentability in International Appln. No. PCT/US2019/064760, dated Jun. 8, 2021, 7 pages.
International Search Report and Written Opinion in International Appln. No. PCT/US2019/064760, dated Apr. 23, 2020, 10 pages.
Kubler et al., "Self-adjuvanted mRNA vaccination in advanced prostate cancer patients: a first-in-man phase I/IIa study," Journal for Immuno Therapy of Cancer, Jun. 2015, 3:26, 14 pages.
Miyauchi et al., "HPV16 E5 Mediates Resistance to PD-L1 Blockade and can be Targeted with Rimantadine in Head and Neck Cancer," Cancer Research, Dec. 2019, 80(4):732-746.
O'Brien et al., "Evasion of host immunity directed by papillomavirus-encoded proteins," Virus Research, Sep. 2002, 88:103-117.
Pardi et al., "mRNA vaccines—a new era in vaccinology," Nature Review—Drug Discovery, Apr. 2018, 17(4): 261-279.
Rausch et al., "mRNA vaccine CV9103 and CV9104 for the treatment of prostate cancer," Human Vaccines & Immunotherapeutics, Nov. 2014, 10(11): 3146-3152.

(Continued)

*Primary Examiner* — Amy L Clark
*Assistant Examiner* — Chihyi Lee
(74) *Attorney, Agent, or Firm* — Fish & Richardson P.C.

(57) ABSTRACT

Provided herein are methods for treating cancer comprising administering to a subject in need thereof an adamantane derivative, or a pharmaceutically acceptable salt thereof, such as rimantadine or amantadine. In some embodiments, the adamantane derivative is PEGylated.

17 Claims, 21 Drawing Sheets

(56) References Cited

OTHER PUBLICATIONS

Seiwert et al., "Safety and clinical activity of pembrolizumab for treatment of recurrent or metastatic squamous cell carcinoma of the head and neck (Keynote-012): an open-label, multicentre, phase 1b trial," Lancet Oncology, Jul. 2016, 17(7):956-965.
Senba et al., "Mechanisms of virus immune evasion lead to development from chronic inflammation to cancer formation associated with human papillomavirus infection," Oncology Reviews, Oct. 2012, 6(2)(e17):135-144.
Venuti et al., "Papillomavirus E5: the smallest oncoprotein with many functions," Molecular Cancer, Nov. 2011, 10:140, 18 pages.
Veronese et al., "PEGylation, successful approach to drug delivery," Drug Discovery Today, Nov. 2005, 10(21):1451-1458.
Hier et al., "A Murine Model for the Immunotherapy of Head and Neck Squamous Cell Carcinoma," The Laryngoscope, Oct. 1995, 105(10):1077-1080.
Office Action in European Appln. No. 19892331.0 mailed on Jan. 16, 2025, 6 pages.
Shindoh et al., "Detection of human papillomavirus DNA sequences in oral squamous cell carcinomas and their relation to p53 and proliferating cell nuclear antigen expression, " Cancer, Nov. 1, 1995, 76(9):1513-1521.
Benevolo et al., "Immunohistochemical expression of p16(INK4a) is predictive of HR-HPV infection in cervical low-grade lesions, " Modern Pathology, Jan. 1, 2006, 19(3):384-391.

* cited by examiner

ANTI-CANCER ACTIVITY OF ADAMANTANE DERIVATIVES

CROSS-REFERENCE TO RELATED APPLICATIONS

This application is a National Stage Application under 35 U.S.C. § 371 and claims the benefit of International Application No. PCT/US2019/064760, filed Dec. 5, 2019, which claims the benefit of U.S. Provisional Application No. 62/775,731, filed Dec. 5, 2018, each of which is incorporated herein by reference in its entirety.

TECHNICAL FIELD

The present disclosure relates to methods of treating cancer comprising administering adamantane or a derivative thereof, for example, rimantadine. The present disclosure more particularly relates to methods of treating cancer comprising administering rimantadine or PEGylated rimantadine.

BACKGROUND

Cancer is the second most common cause of death in the United States. In 2018, approximately 1.7 million new cases were expected to be diagnosed and about 610,000 deaths due to cancer were expected to occur in the United States. There are more than 100 types of cancer including head and neck cancer, skin cancer (e.g., melanoma), cervical cancer, lung cancer, and breast cancer. Head and neck cancer accounts for approximately 4% of all cancers in the United States, and while melanoma accounts for only 1% of skin cancers, it causes the majority of deaths due to skin cancer. Additionally, about 1 in 8 women in the United States will develop breast cancer over the course of her lifetime, and death rates due to breast cancer are higher for women than any other cancer, excluding lung cancer. Additionally, about 5% of overall cancer worldwide is associated with human papillomavirus (HPV), including cervical cancer and head and neck squamous cell carcinoma (HNSCC), and the percentage of HPV-associated cancer has been increasing. Anti-PD-1 checkpoint blockade immunotherapy for recurrent or metastatic HNSCC after platinum-based chemotherapy was approved by the FDA due to overall survival benefits in patients receiving these anti-PD-1 agents, but the objective response rate to single agent checkpoint blockade immunotherapy in remains low (see e.g., Ferris et al. *N Engl J Med.* 2016 Nov. 10; 375(19): 1856-1867; Seiwert et al. *Lancet Oncol.* 2016 July; 17(7):956-965; Cohen et al. *Lancet.* 2019 Jan. 12; 393(10167): 156-167; each of which is incorporated by reference herein in its entirety). Thus, there remains a need to provide drugs to treat cancer.

SUMMARY

Provided herein are methods of treating cancer in a subject in need thereof, the methods comprising administering to the subject a therapeutically effective amount of an adamantane derivative (i.e., one or more adamantane derivatives), or a pharmaceutically acceptable salt thereof.

In some embodiments, the adamantane derivative is a compound of Formula I:

I

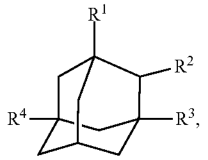

or a pharmaceutically acceptable salt thereof, wherein:

$R^1$ is H, —$NH_2$, or alkyl optionally substituted with —$NH_2$;

$R^2$ is H or —$NH_2$ optionally substituted with phenyl, wherein the phenyl is optionally substituted with one or more halogen atoms; and $R^3$ and $R^4$ are independently selected from H and $C_1$-$C_3$ alkyl;

wherein when $R^2$ is not H, $R^1$ is H; and wherein at least one of $R^1$, $R^2$, $R^3$, and $R^4$ is not H.

In some embodiments, the adamantane derivative, or a pharmaceutically acceptable salt thereof, is selected from the group consisting of: rimantadine, amantadine, tromantadine, adapromine, memantine, bromantane, or a combination thereof, or a pharmaceutically acceptable salt thereof.

In some embodiments, the adamantane derivative is rimantadine, or a pharmaceutically acceptable salt thereof; amantadine, or a pharmaceutically acceptable salt thereof; or a combination thereof. In some embodiments, the adamantane derivative is rimantadine, or a pharmaceutically acceptable salt thereof. In some embodiments, the adamantane derivative is amantadine, or a pharmaceutically acceptable salt thereof.

In some embodiments, the adamantane derivative, or pharmaceutically acceptable salt thereof, is PEGylated. In some embodiments, the PEG is a high molecular weight PEG. In some embodiments, the PEG is a low molecular weight PEG.

In some embodiments, the adamantane derivative, or a pharmaceutically acceptable salt thereof, is modified. In some embodiments, the modification is PEGylation. In some embodiments, the PEGylated adamantane derivative, or a pharmaceutically acceptable salt thereof, is PEGylated with a high molecular weight PEG. In some embodiments, the PEGylated adamantane derivative, or a pharmaceutically acceptable salt thereof, is PEGylated with a low molecular weight PEG.

In some embodiments, the PEGylated adamantane derivative is PEGylated rimantadine, or a pharmaceutically acceptable salt thereof. In some embodiments, the PEGylated rimantadine, or a pharmaceutically acceptable salt thereof, is PEGylated with a high molecular weight PEG. In some embodiments, the PEGylated rimantadine, or a pharmaceutically acceptable salt thereof, is PEGylated with a low molecular weight PEG.

In some embodiments, the PEGylated adamantane derivative is PEGylated amantadine. In some embodiments, the PEGylated amantadine, or a pharmaceutically acceptable salt thereof, is PEGylated with a high molecular weight PEG. In some embodiments, the PEGylated amantadine, or a pharmaceutically acceptable salt thereof, is PEGylated with a low molecular weight PEG.

In some embodiments, the subject is administered a pharmaceutically acceptable salt of the adamantane derivative. In some embodiments, the pharmaceutically acceptable salt of the adamantane derivative is a hydrochloride salt.

Also provided herein are methods of treating cancer in a subject in need thereof, the methods comprising administering to the subject a therapeutically effective amount of rimantadine, or a pharmaceutically acceptable salt thereof.

In some embodiments, the subject is administered a pharmaceutically acceptable salt of rimantadine. In some embodiments, the pharmaceutically acceptable salt is a hydrochloride salt.

In some embodiments, the subject is administered a pharmaceutically acceptable salt of memantine. In some embodiments, the pharmaceutically acceptable salt is a hydrochloride salt.

In some embodiments, the rimantadine, or pharmaceutically acceptable salt thereof, is PEGylated. In some embodiments, the PEGylated rimantadine, or pharmaceutically acceptable salt thereof, comprises a high molecular weight PEG. In some embodiments, the PEGylated rimantadine, or pharmaceutically acceptable salt thereof, comprises a low molecular weight PEG.

In some embodiments, the rimantadine, or a pharmaceutically acceptable salt thereof, is modified. In some embodiments, the modification is PEGylation. In some embodiments, the PEGylated rimantadine, or a pharmaceutically acceptable salt thereof, is PEGylated with a high molecular weight PEG. In some embodiments, the PEGylated rimantadine, or a pharmaceutically acceptable salt thereof, is PEGylated with a low molecular weight PEG. Accordingly, also provided herein are methods of treating cancer in a subject in need thereof, the method comprising administering to the subject a therapeutically effective amount of PEGylated rimantadine, or a pharmaceutically acceptable salt thereof.

In some of any of the above embodiments, the cancer is a sarcoma, carcinoma, melanoma, lymphoma, or leukemia. In some embodiments, the cancer is a carcinoma. In some embodiments, the carcinoma is selected from the group consisting of: an adenocarcinoma, a squamous cell carcinoma, a transitional cell carcinoma, and a clear cell carcinoma. In some embodiments, the cancer is a squamous cell carcinoma. In some embodiments, the squamous cell carcinoma is head and neck squamous cell carcinoma (HNSCC).

In some embodiments, the cancer is selected from the group consisting of: head and neck cancer, breast cancer, and melanoma.

In some embodiments, one or more cancer cells from the subject express a human papilloma virus (HPV) protein. In some embodiments, the HPV protein is one or more of an HPV E5, E6, or E7 protein. In some embodiments, the HPV E5, E6, or E7 protein is from one or more HPV subtypes selected from the group consisting of: HPV 6, HPV 11, HPV 16, HPV 18, HPV 31, HPV 33, HPV 35, HPV 39, HPV 45, HPV 51, HPV 52, HPV 56, HPV 58, HPV 66, and HPV 69.

In some embodiments, the HPV protein is HPV16 E5. In some embodiments, the cancer is an HPV-associated cancer.

Also provided herein are methods of treating cancer (e.g., any of the cancers described herein) in a subject in need thereof, the method comprising: (a) detecting in a sample from the subject a cancer cell that expresses a HPV protein (e.g., HPV E5, HPV E6, HPV E7, or a combination thereof); and (b) administering to the subject a therapeutically effective amount of rimantadine, or a pharmaceutically acceptable salt thereof. In some embodiments, the cancer is selected from the group consisting of: head and neck cancer, a mucosal squamous cell carcinoma, a cutaneous squamous cell carcinoma, cervical cancer, vaginal cancer, vulvar cancer, penile cancer, and anal cancer.

In some of any of the above embodiments, the methods further comprise administering an additional anti-cancer agent. In some embodiments, the additional anti-cancer agent is selected from the group consisting of: carboplatin, cisplatin, gemcitabine, methotrexate, paclitaxel, pemetrexed, lomustine, temozolomide, dacarbazine, and a combination thereof. In some embodiments, the additional anti-cancer agent is an immunotherapy. In some embodiments, the additional anti-cancer agent is an immune checkpoint inhibitor. In some embodiments, the immune checkpoint inhibitor targets one or more of: CTLA-4, PD-1, PD-L1, BTLA, LAG-3, A2AR, TIM-3, B7-H3, VISTA, and IDO. In some embodiments, the immune checkpoint inhibitor is selected form the group consisting of: ipilimumab, nivolumab, pembrolizumab, atezolizumab, avelumab, durvalumab, cemiplimab-rwlc, tremelimumab, cemiplimab, and a combination thereof. In some embodiments, the methods further comprise subjecting the subject to radiation therapy, surgery, or a combination thereof.

In some embodiments, the subject is a human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, databases entries, and other references mentioned herein are incorporated by reference in their entirety. In case of conflict, the present specification, including definitions, will control.

DESCRIPTION OF DRAWINGS

FIG. 1A shows the tumor volumes of mice (n=6 per group) inoculated with $5\times10^5$ AT84-E7-E5 tumor cells and treated with IP injections of 10 mg/kg body weight rimantadine once daily for a total of 7 injections starting on day 8. FIG. 1B shows the tumor volumes of mice (n=6 per group) inoculated with $1.5\times10^5$ B16-OVA tumor cells and treated with IP injections of 10 mg/kg body weight rimantadine once daily for a total of 7 injections starting on day 10. FIG. 1C shows the tumor volumes of mice (n=5 per group) inoculated with $5\times10^5$ 4T1 tumor cells and treated with IP injections of 10 mg/kg body weight rimantadine once daily for a total of 7 injections starting on day 6. FIG. 1D shows the tumor volumes of mice (n=6 per group) inoculated with $1.0\times10^6$ 4MOSC1 tumor cells and treated with IP injections of 10 mg/kg body weight rimantadine once daily for a total of 7 injections starting once tumors were palpable. FIG. 1E shows the tumor volumes of mice (n=6 per group) inoculated with $1.5\times10^5$ B16-OVA tumor cells and treated with IP injections of 10 mg/kg body weight PEGylated Rimantadine (PEG-Rim) once daily for a total of 7 injections starting on day 10.

FIG. 2A shows the tumor volumes of mice (n=6 per group) inoculated with $5\times10^5$ AT-84-E7 cells expressing empty vector and treated with rimantadine for one week. FIG. 2B shows the tumor volumes of mice (n=6 per group) inoculated with $5\times10^5$ AT-84-E7 cells expressing FLAG-tagged E5 and treated with rimantadine for one week.

Figure 3A:
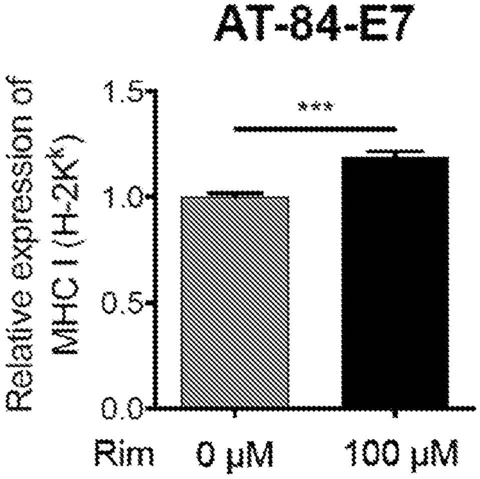
Figure 3B:
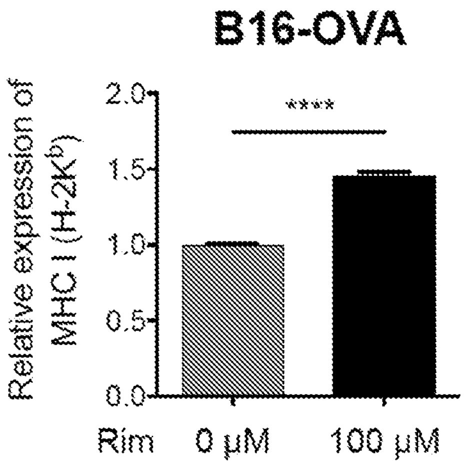
Figure 3C:
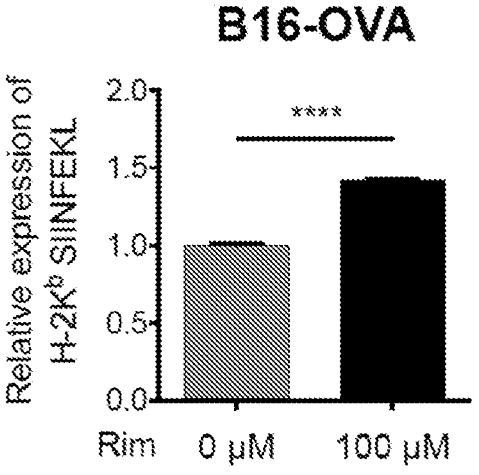
Figure 3D:
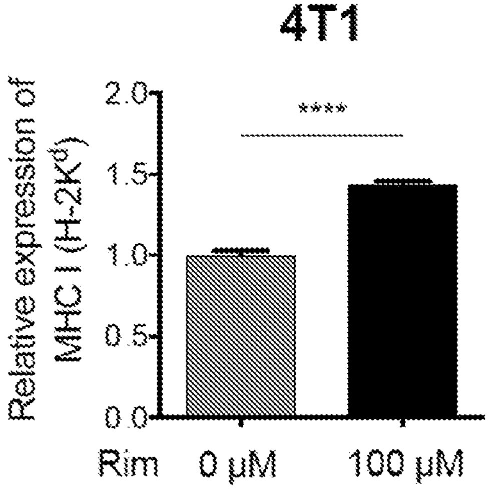
Figure 3E:
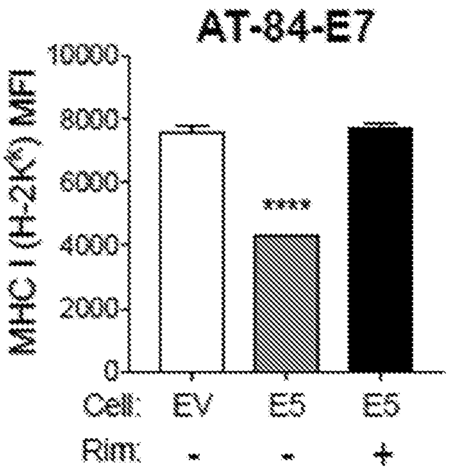

FIGS. 3A-3E are plots showing MHC I expression or antigen-presentation (H-2Kb/SIINFEKL) as analyzed by flow cytometry after rimantadine treatment (100 μM, 48 hours). FIG. 3A is a plot showing MHC I expression for the AT-84-E7 model. FIG. 3B is a plot showing MHC I expression for the B16-OVA model. FIG. 3C is a plot showing antigen-presentation (H-2Kb/SIINFEKL) for the B16-OVA model. FIG. 3D is a plot showing MHC I expression for the 4T1 model. FIG. 3E is a plot showing restoration of expression of MHC I on E5-positive AT-84-E7 with rimantadine treatment.

Figure 4A:
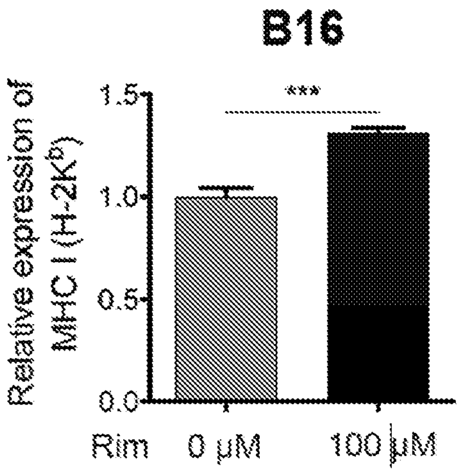
Figure 4B:
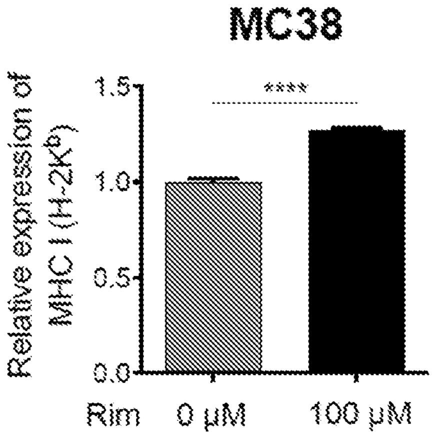
Figure 4C:
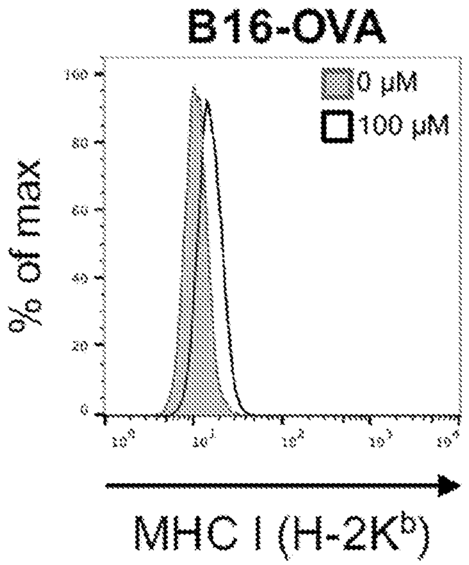
Figure 4D:
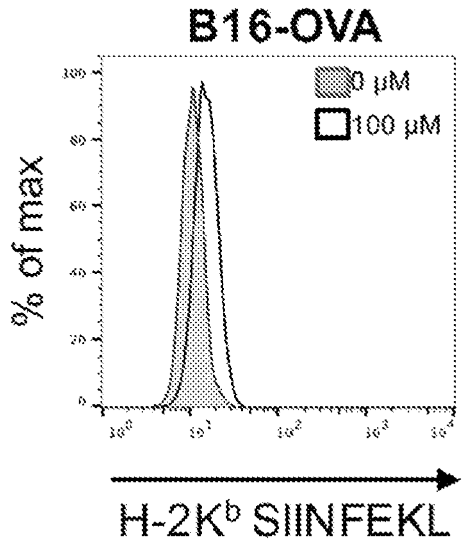

FIGS. 4A-4D are plots showing MHC expression in tumor cells. FIGS. 4A and 4B show MHC I expression analyzed by flow cytometry 48 hours after rimantadine treatment for B16 and MC38 cells, respectively. FIGS. 4C and 4D are plots showing expression of MHC I and antigen presentation (H-2Kb/SIINFEKL), respectively, 24 hours after rimantadine treatment in B16-OVA cells.

Figure 5:
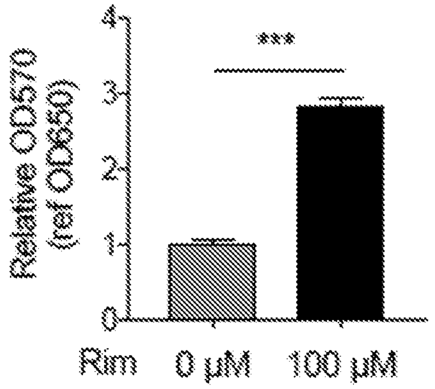

FIG. 5 is a plot showing B3Z activation after rimantadine treatment (48 hours).

Figure 6:
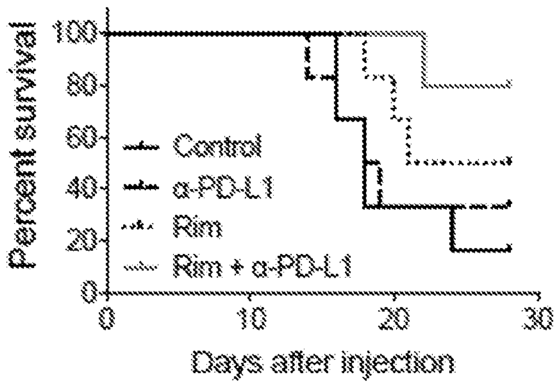

FIG. 6 is a plot showing the survival curve of B16-OVA-bearing mice treated with rimantadine and/or anti-PD-L1 antibody; n=6 in each group.

Figure 7A:
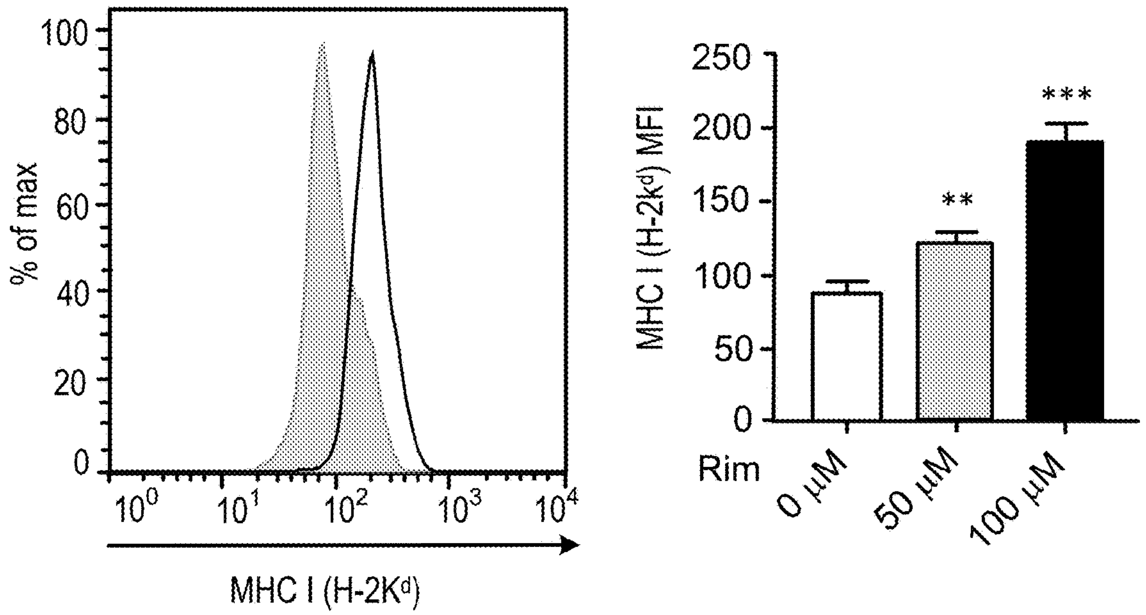
Figure 7B:
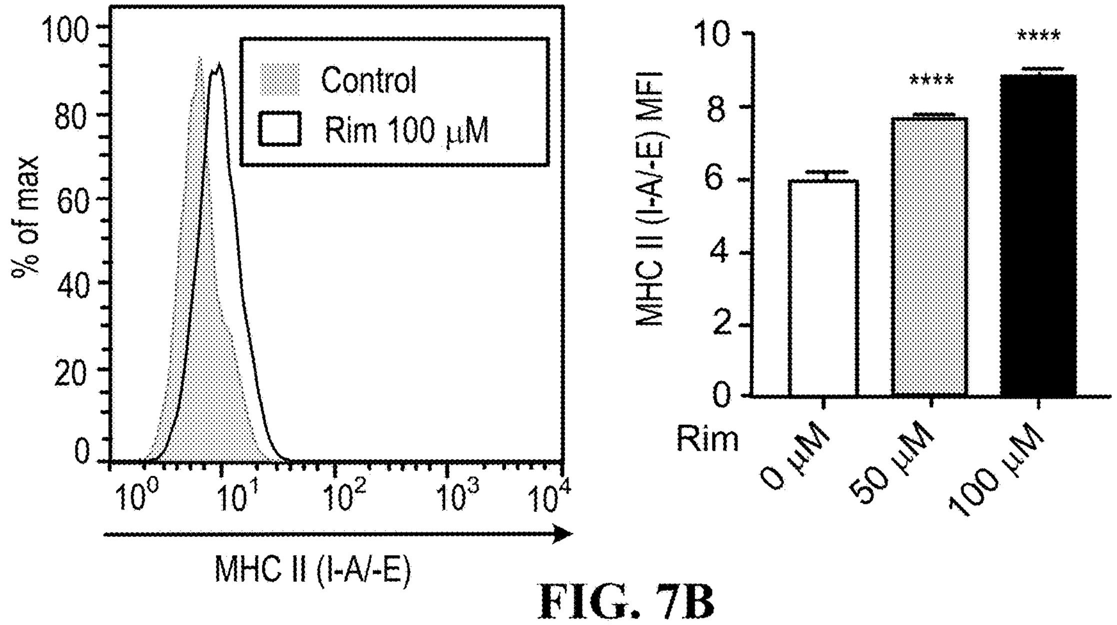

FIGS. 7A and 7B are plots showing cell surface expression of MHC I (H-2Kd) and MHC II (I-A/I-E), respectively, on rimantadine-treated RAW264.7 48 hours after treatment. Data are shown as mean±S.E.M. Statistics were done using an unpaired t-test.

Figure 8:
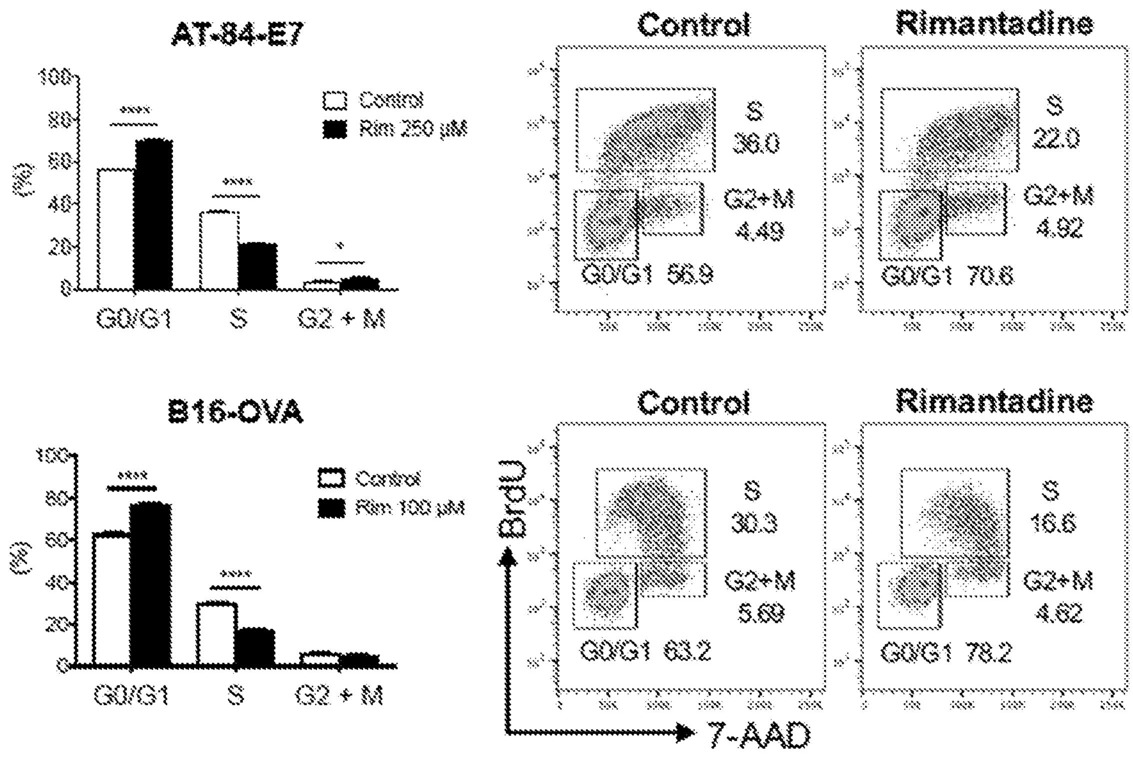
Figure 9:
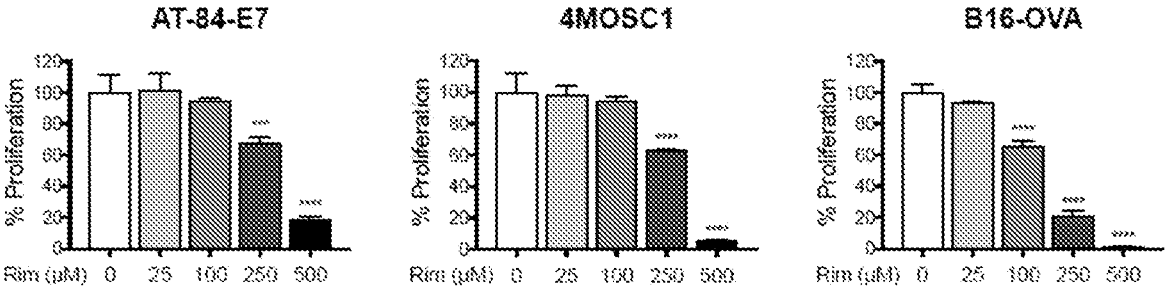

FIG. 8 has plots showing the BrdU cell cycle analyzed for 24 hours following treatment with rimantadine, FIG. 9 has plots showing the cell proliferation assay (MTT), which was analyzed 48 hours following treatment with rimantadine. Data are shown as mean±S.E.M. Statistics were done using an unpaired t-test or one-way ANOVA.

Figure 10A:
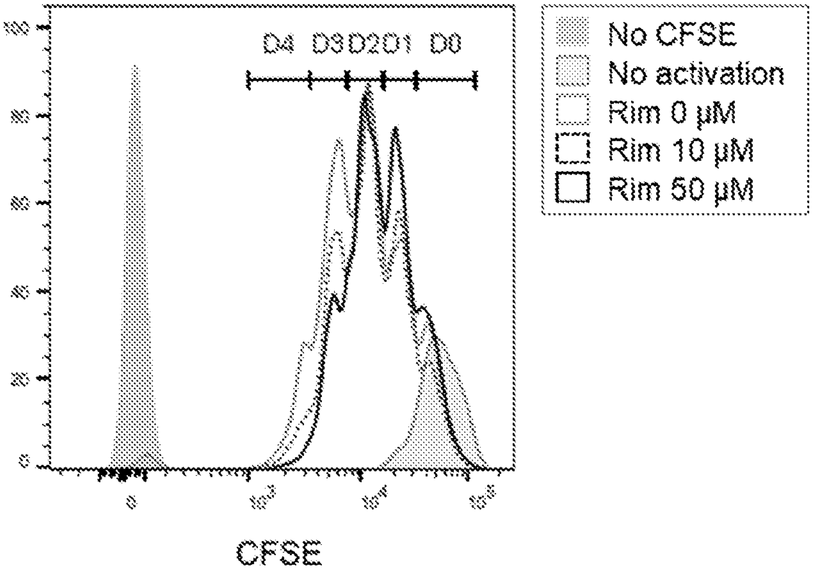
Figure 10B:
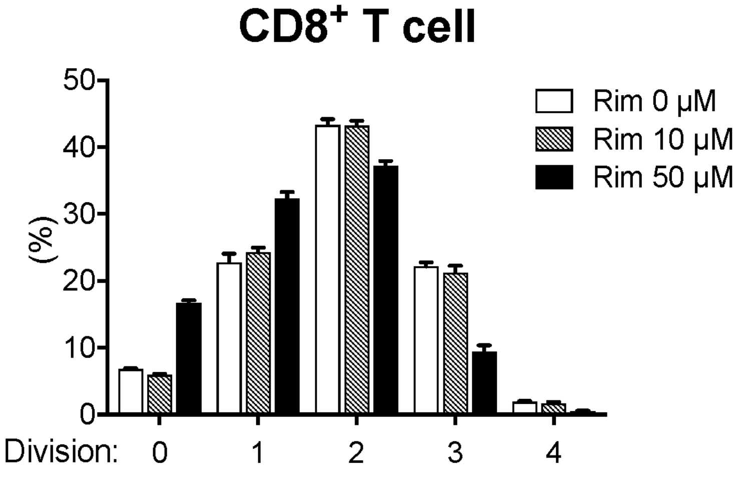

FIGS. 10A and 10B are plots showing T-cell proliferation assay using CFSE-labeled T-cells simulated to proliferate in the presence or absence of rimantadine.

Figure 11A:
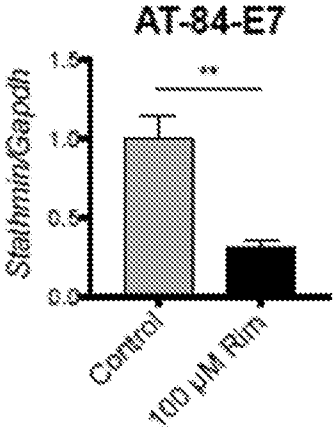
Figure 11B:
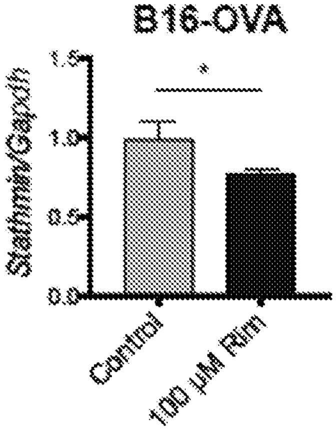

FIGS. 11A and 11B are plots showing Stathmin mRNA expression, which was analyzed 24 hours following treatment with rimantadine in AT-84-E7 cells and B16-OVA cells, respectively.

Figure 12A:
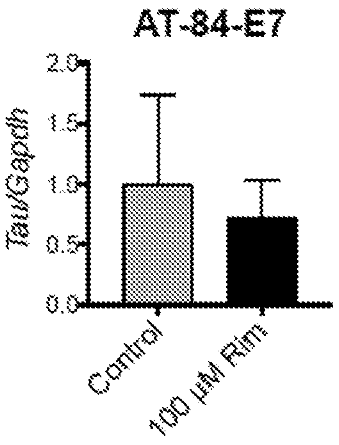
Figure 12B:
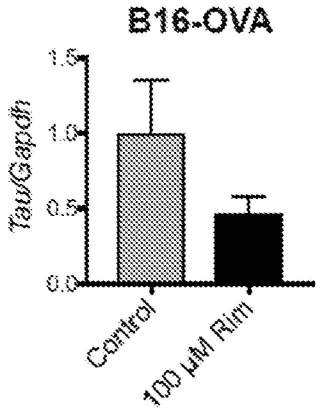

FIGS. 12A and 12B are plots showing Tau mRNA expression, which was analyzed 24 hours following treatment with rimantadine. Data are shown as mean±S.E.M. Statistics were done using an unpaired 1-test or one-way ANOVA.

Figure 13:
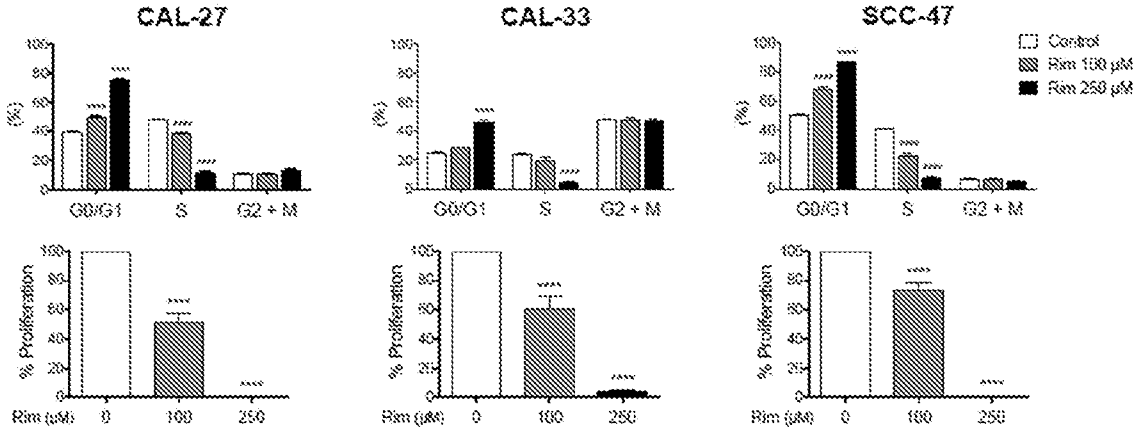

FIG. 13 has plots showing the effect of rimantadine on human HNSCC lines as labeled. BrdU cell cycle analysis (upper) and MTT proliferation assay (lower).

Figure 14:
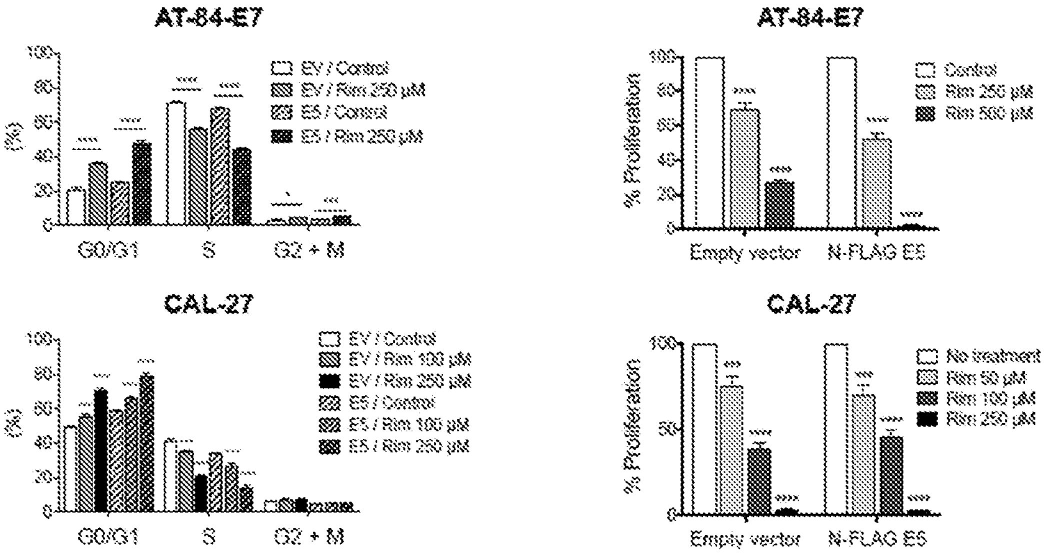

FIG. 14 has plots showing cell cycle and proliferation assay data of E5-expressing cell lines. Cells were treated with rimantadine for 24 hours for BrdU assay and qPCR analysis, or for 48 hours for MTT assay at the concentration as indicated. Experiment repeated twice with similar results. Data are shown as mean±S.E.M. Statistics were done using an unpaired t-test or one-way ANOVA.

Figure 15:
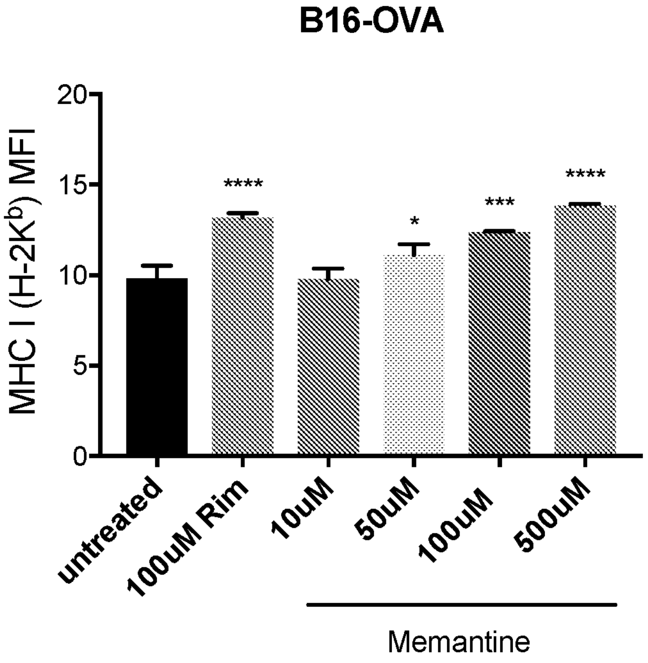

FIG. 15 is a plot showing MHC I expression after memantine treatment (24 hours at indicated concentrations) in B16-OVA cells.

Figure 16A:
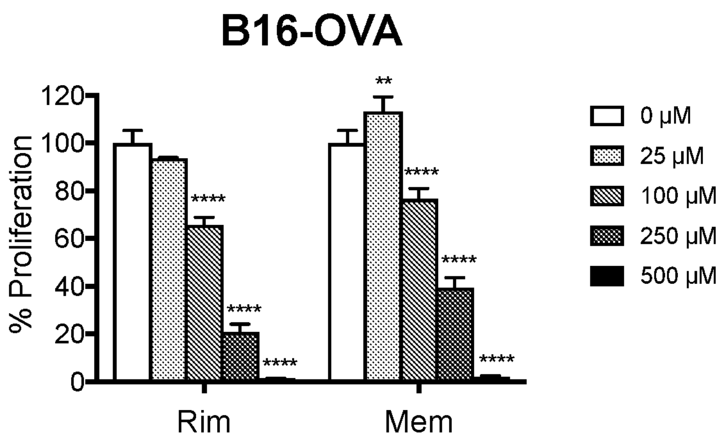
Figure 16B:
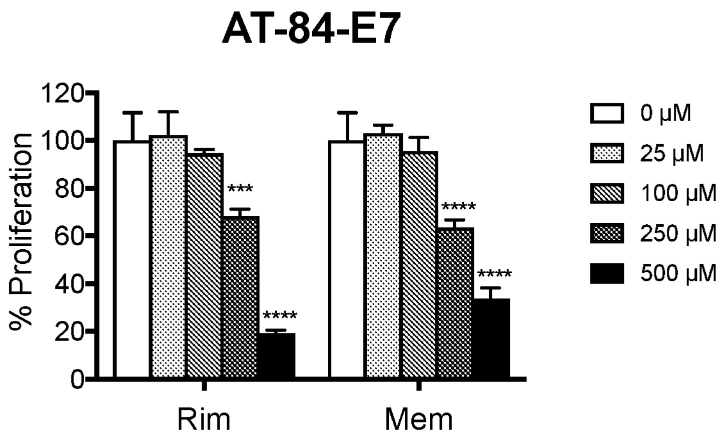
Figure 16C:
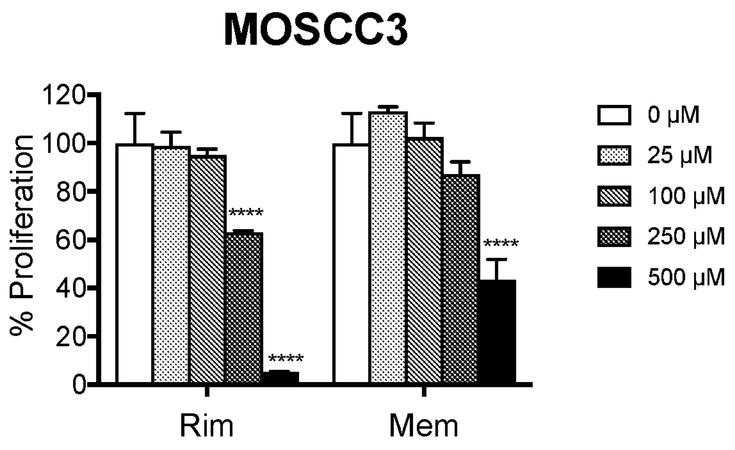

FIGS. 16A to 16C are plots showing cell proliferation assays (MTT), which were analyzed 48 hours following treatment with rimantadine or memantine for B16-OVA (FIG. 16A), AT-84-E7 (FIG. 16B), and MOSCC3 (FIG. 16C) cell lines. Data are shown as mean±S.E.M. Statistics were done using an unpaired 1-test or one-way ANOVA.

Figure 17A:
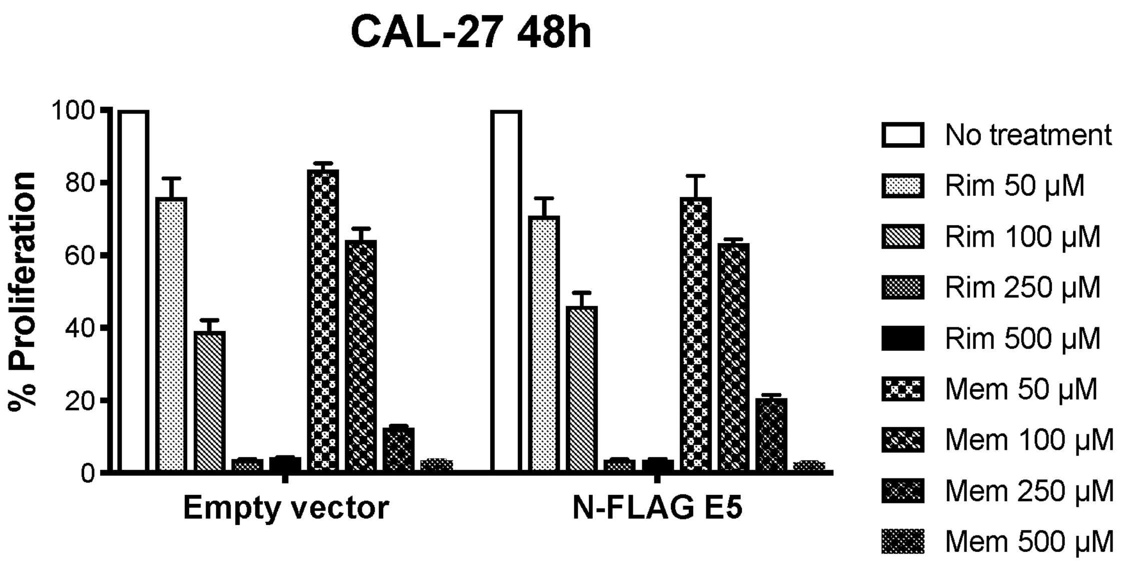
Figure 17B:
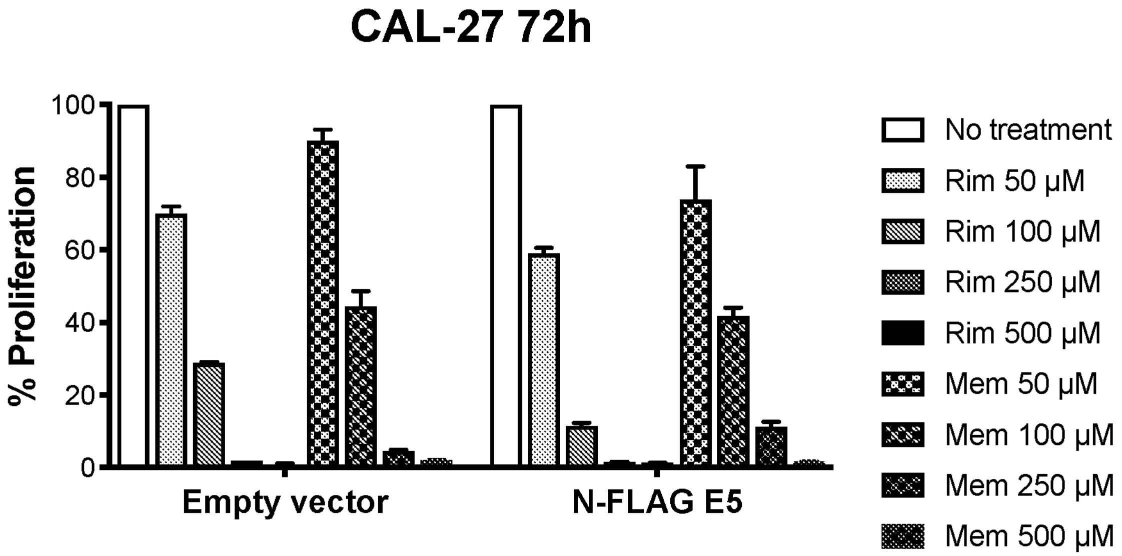

FIGS. 17A and 17B are plots showing the cell proliferation assay (MTT) for CAL-27 cells treated with rimantadine or memantine. The proliferation was measured at 48 hours (FIG. 17A) and 72 hours (FIG. 17B).

DETAILED DESCRIPTION

Definitions

As used herein, the terms "subject," "individual," or "patient," used interchangeably, refer to any animal, including mammals such as mice, rats, other rodents, rabbits, dogs, cats, swine, cattle, sheep, horses, primates, and humans. In some embodiments, the subject is a human.

As used herein, the terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

The term "preventing" as used herein means the prevention of the onset, recurrence or spread, in whole or in part, of the disease or condition as described herein, or a symptom thereof.

The term "administration" or "administering" refers to a method of giving a dosage of a compound or pharmaceutical composition to a vertebrate or invertebrate, including a mammal, a bird, a fish, or an amphibian. The preferred method of administration can vary depending on various factors, e.g., the components of the pharmaceutical composition, the site of the disease, and the severity of the disease.

By "therapeutically effective amount" or "pharmaceutically effective amount" of a compound as provided herein is an amount which is sufficient to achieve the desired effect and can vary according to the nature and severity of the disease condition, and the potency of the compound. A therapeutic effect is the relief, to some extent, of one or more of the symptoms of the disease, and can include curing a disease. "Curing" means that the symptoms of active disease are eliminated. However, certain long-term or permanent effects of the disease can exist even after a cure is obtained (such as, e.g., extensive tissue damage).

The term "regulatory agency" refers to a country's agency for the approval of the medical use of pharmaceutical agents with the country. For example, a non-limiting example of a regulatory agency is the U.S. Food and Drug Administration (FDA).

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

As used herein, the term "pharmaceutically acceptable salt" refers to a salt that retains the desired biological activity of the subject compound and exhibits minimal undesired toxicological effects. The pharmaceutically acceptable salt may be prepared in situ during the final isolation and purification of the compound, or by separately reacting the purified compound in its free acid or free base form with a suitable base or acid, respectively. In some embodiments, a pharmaceutically acceptable salt can be preferred over the respective free base or free acid because such a salt imparts greater stability or solubility to the molecule thereby facilitating formulation into a dosage form. Basic compounds are generally capable of forming pharmaceutically acceptable acid addition salts by treatment with a suitable acid. Suitable acids include pharmaceutically acceptable inorganic acids and pharmaceutically acceptable organic acids. Non-limiting examples of a pharmaceutically acceptable acid addition salt include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), napthalene-2-sulfonate, ethanedisulfonate, and 2,5-dihydroxybenzoate.

The term "alkyl" refers to a saturated linear or branched-chain monovalent hydrocarbon radical. For example, "alkyl" can include "$C_1$-$C_3$ alkyl", "$C_3$-$C_6$ alkyl", "$C_1$-$C_6$ alkyl", and "$C_2$-$C_6$ alkyl", which can refer to saturated linear or branched-chain monovalent hydrocarbon radicals of one to three, three to six, one to six, or two to six carbon atoms, respectively. Examples include, but are not limited to, methyl, ethyl, 1-propyl, isopropyl, 1-butyl, isobutyl, sec-butyl, tert-butyl, 2-methyl-2-propyl, pentyl, neopentyl, and hexyl.

The term "halogen" includes fluoro, chloro, bromo and iodo.

In some embodiments, the term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

Methods of Treatment

Adamantane derivatives have been used to prevent and treat influenza A virus infections for many years. For example, the adamantane derivatives amantadine (SYMMETREL™) and rimantadine (FLUMADINE™) have been used for influenza A virus infections for more than 30 years. These antiviral drugs are thought to function in this capacity through inhibition of the matrix-2 (M2) protein, a proton-selective viroporin. More recently, other adamantane derivatives, such as memantine (EBIXA®, NAMENDA®), have been used to treat neurodegenerative disorders such as Parkinson's disease and Alzheimer's disease. These compounds are thought to inhibit the N-methyl-D-aspartate (NMDA) receptor, which is involved in synaptic plasticity and memory function. Unexpectedly, the present inventors discovered that adamantane derivatives, rimantadine, and PEGylated rimantadine, have anti-cancer activity. Accordingly, the present disclosure provides methods of treating cancer that comprise administering a therapeutically effective amount of one or more adamantane derivatives, for example, rimantadine, amantadine, or derivatives thereof.

Adamantane is a compound with the following formula:

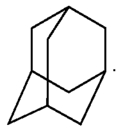

As referred to herein, an "adamantane derivative" is a compound having an adamantyl core. Non-limiting examples of adamantane derivatives include rimantadine, amantadine, tromantadine, adapromine, memantine, and bromantane, which have the following structures:

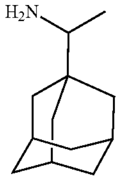

rimantadine

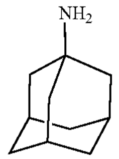

amantadine

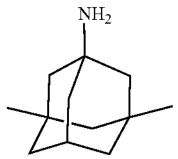

memantine

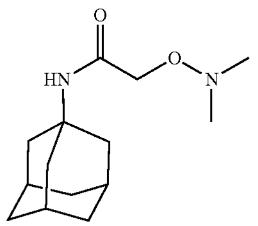

tromantadine

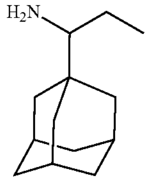

adapromine

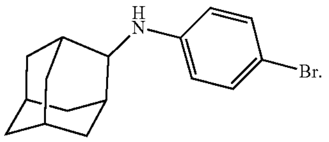

bromantane

As another example, an adamantane derivative can be a compound of Formula I:

I

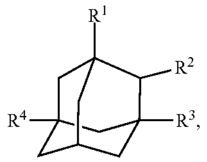

or a pharmaceutically acceptable salt thereof, wherein:

$R^1$ is H, —$NH_2$, or alkyl optionally substituted with —$NH_2$;

$R^2$ is H or —$NH_2$ optionally substituted with phenyl, wherein the phenyl is optionally substituted with one or more halogen atoms; and $R^3$ and $R^4$ are independently selected from H and $C_1$-$C_3$ alkyl;

wherein when $R^2$ is not H, $R^1$ is H; and wherein at least one of R1, R2, R3, and R4 is not H.

Further non-limiting examples of adamantane derivatives include the compounds disclosed in U.S. Pat. No. 5,061,703 and U.S. Publication No. 2018/0215699; each of which is incorporated herein by reference in its entirety.

In some embodiments, an adamantane derivative is a compound with an adamantyl core that increases major histocompatibility complex (MHC) expression on a tumor cell and/or an antigen presenting cell. For example, an adamantane derivative can be determined to increase MHC expression (e.g., MHC class I and/or MHC class II) on a tumor cell and/or an antigen presenting cell using an assay as described in Miyauchi et al. "HPV16 E5 Mediates Resistance to PD-L1 Blockade and Novel Anti-tumor Activity of Rimantadine in Head and Neck Cancer," to be published in *Cancer Res*. late 2019; which is incorporated herein by reference in its entirety. In some embodiments, an adamantane derivative is a compound with an adamantyl core that inhibits one or more cell cycle regulatory proteins. For example, an adamantane derivative can be determined to inhibit one or more cell cycle regulatory proteins using an assay as described in Miyauchi et al. "HPV16 E5 Mediates Resistance to PD-L1 Blockade and Novel Anti-tumor Activity of Rimantadine in Head and Neck Cancer," to be published in *Cancer Res*. late 2019. In some embodiments, an adamantane derivative is a compound having an adamantyl core that can inhibit HPV16 E5. In some embodiments, an adamantane derivative is a compound having an adamantyl core that can bind to the M2 protein. In some embodiments, an adamantane derivative is a compound having an adamantyl core and NMDA antagonistic properties.

In some embodiments, an adamantane derivative, or pharmaceutically acceptable salt thereof, has a molecular weight of about 130 g/mol to about 500 g/mol. For example, about 130 g/mol to about 200 g/mol, about 130 g/mol to about 250 g/mol, about 130 g/mol to about 300 g/mol, about 130 g/mol to about 350 g/mol, about 130 g/mol to about 400 g/mol, about 130 g/mol to about 450 g/mol, about 450 g/mol to about 500 g/mol, about 400 g/mol to about 500 g/mol, about 350 g/mol to about 500 g/mol, about 300 g/mol to about 500 g/mol, about 250 g/mol to about 500 g/mol, or about 200 g/mol to about 500 g/mol.

In some embodiments, a method as described herein comprises administering rimantadine, or a pharmaceutically acceptable salt thereof. In some embodiments, the method comprises administering amantadine, or a pharmaceutically acceptable salt thereof.

In some embodiments, an adamantane derivative as described herein is PEGylated. As used herein, "PEGylated" or "PEGylation" describes the conjugation of a compound with a polyethylene glycol (PEG) moiety. The PEG moiety can be of any length. For example, the PEG moiety can have from 2 to 500 repeating units. In some embodiments, the PEG moiety can have an average molecular weight of about 300 g/mol to about 10,000,000 g/mol. In some embodiments, the PEG moiety can be a high molecular weight PEG or low molecular weight PEG. For example, a high molecular weight PEG has a molecular weight greater than or equal to 5 kDa, and a low molecular weight PEG has a molecular weight of less than 5 kDa. In some embodiments, the PEG is selected from the group consisting of: PEG 200, PEG 300, PEG 400, PEG 600, PEG 800, PEG 1000, PEG 1500, PEG 2000, and PEG 3350. A PEG moiety can be a linear PEG or the PEG moiety can be a branched PEG. For example, branched PEGs includes any PEG having one or more branches of PEG groups extending from a PEG backbone.

In some embodiments, a PEGylated adamantane derivative, or pharmaceutically acceptable salt thereof, has a molecular weight of about 300 g/mol to about 10,000 g/mol. For example, about 300 g/mol to about 500 g/mol, about 300 g/mol to about 1000 g/mol, about 300 g/mol to about 1500 g/mol, about 300 g/mol to about 2000 g/mol, about 300 g/mol to about 2500 g/mol, about 300 g/mol to about 3000 g/mol, about 300 g/mol to about 3500 g/mol, about 300 g/mol to about 4000 g/mol, about 300 g/mol to about 4500 g/mol, about 300 g/mol to about 5000 g/mol, about 300 g/mol to about 5500 g/mol, about 300 g/mol to about 6000 g/mol, about 300 g/mol to about 7000 g/mol, about 300 g/mol to about 8000 g/mol, about 300 g/mol to about 9000 g/mol, about 9000 g/mol to about 10,000 g/mol, about 8000 g/mol to about 10,000 g/mol, about 7000 g/mol to about 10,000 g/mol, about 6000 g/mol to about 10,000 g/mol, about 5000 g/mol to about 10,000 g/mol, about 4000 g/mol to about 10,000 g/mol, about 3000 g/mol to about 10,000 g/mol, about 2000 g/mol to about 10,000 g/mol, or about 1000 g/mol to about 10,000 g/mol. In some embodiments, a PEGylated adamantane derivative, or pharmaceutically acceptable salt thereof, has a molecular weight of about 500 g/mol to about 1500 g/mol, about 1000 g/mol to about 2500 g/mol, or about 1500 g/mol to about 3000 g/mol. In some embodiments, a PEGylated adamantane derivative, or pharmaceutically acceptable salt thereof, has a molecular weight of about 300 g/mol to about 1000 g/mol, e.g., about 300 g/mol to about 500 g/mol, about 400 g/mol to about 600 g/mol, about 500 g/mol to about 700 g/mol, about 600 g/mol to about 800 g/mol, about 700 g/mol to about 900 g/mol, or about 800 g/mol to about 1000 g/mol).

In some embodiments, the cancer is a sarcoma, carcinoma, melanoma, lymphoma, or leukemia. Non-limiting examples of a sarcoma include: bone sarcoma (e.g., angiosarcoma, fibrosarcoma, liposarcoma, chondrosarcoma, chordoma, Ewing's sarcoma, giant cell tumor, osteosarcoma, rhabdomyosarcoma, and synovial sarcoma) and soft tissue sarcoma (e.g., fibrosarcoma, gastrointestinal stromal tumor (GIST), Kaposi's sarcoma, leiomyosarcoma, liposarcoma, rhabdomyosarcoma, and soft tissue Ewing's sarcoma). Non-limiting examples of a carcinoma include: basal cell carcinoma, squamous cell carcinoma, renal cell carcinoma, invasive ductal carcinoma, and adenocarcinoma. Non-limiting examples of lymphoma include: Non-Hodgkin's lymphoma (e.g., B-cell lymphoma, T-cell lymphoma, Burkitt's lymphoma, follicular lymphoma, mantle cell lymphoma, primary mediastinal B-cell lymphoma, small lymphocytic lymphoma, Waldenstrom macroglobulinemia) and Hodgkin's lymphoma (e.g., lymphocyte-depleted Hodgkin's disease, lymphocyte-rich Hodgkin's disease, mixed cellularity Hodgkin's lymphoma, nodular lymphocyte-predominant Hodgkin's disease, and nodular sclerosis Hodgkin's lymphoma). Non-limiting examples of leukemia include: acute hairy cell leukemia, acute lymphocytic leukemia, acute myeloid leukemia, acute promyelocytic leukemia, chronic lymphocytic leukemia, chronic myeloid leukemia, a myeloproliferative neoplasm, and systemic mastocytosis.

In some embodiments, the cancer is selected from the group consisting of: melanoma, head and neck cancer, lung cancer, colon cancer, anal cancer, breast cancer, esophageal cancer, pancreatic cancer, prostate cancer, cervical cancer, and stomach cancer. In some embodiments, the cancer is a carcinoma. In some embodiments, the carcinoma is selected from the group consisting of: an adenocarcinoma, a squamous cell carcinoma, a transitional cell carcinoma, and a clear cell carcinoma. In some embodiments, the cancer is a squamous cell carcinoma. In some embodiments, the squamous cell carcinoma is head and neck squamous cell carcinoma.

In some embodiments, the cancer is selected from the group consisting of: head and neck cancer, breast cancer, and melanoma.

In some embodiments, an adamantane derivative, or pharmaceutically acceptable salt thereof, as described herein can be used to treat a human papillomavirus (HPV)-associated cancer in a subject. An "HPV-associated cancer" as used herein is a cancer in which one or more of the cancerous cells express at least one HPV protein. For example, one or more of the cancerous cells can express a HPV oncoprotein. Human papillomavirus (HPV) can cause malignant transformation by, for example, targeting the critical tumor suppressors p53 and Rb (see, e.g., Conway and Meyers. *J Dent Res.* 2009 April; 88(4): 307-17; and Hoppe-Seyler. *Trends Microbiol.* 2018 February; 26(2): 158-168). HPV genes can also help HPV-infected cells evade immune responses (see, e.g., Senba. *Oncol Rev.* 2012 Oct. 5; 6(2): e17). For example, HPV genes and proteins can target the antigen processing and antigen presentation required for effective adaptive immune responses (see, e.g., Senba. *Oncol Rev.* 2012 Oct. 5; 6(2):e17; and O'Brien and Saveria Campo. *Virus Res.* 2002 September; 88(1-2):103-17). There are many HPV oncoproteins including, but not limited to, HPV16 E5, E6, and E7. For example, HPV E5 is protein that has been reported to have multiple functions including regulation of tumor cell differentiation and apoptosis, modulation of H+ ATPase responsible for acidification of late endosomes, and immune modulation including direct binding and downregulation of major histocompatibility complex (MHC) class I and MHC class II (see e.g., *Vemiti. Mol Cancer.* 2011 Nov. 11; 10:140), which can affect antigen processing and presentation.

In some embodiments, one or more cancer cells from the subject express an HPV protein. In some embodiments, the HPV protein is one or more of an HPV E5, E6, or E7 protein. In some embodiments, the HPV E5, E6, or E7 protein is from one or more HPV subtypes selected from the group consisting of: HPV 6, HPV 11, HPV 16, HPV 18, HPV 31, HPV 33, HPV 35, HPV 39, HPV 45, HPV 51, HPV 52, HPV 56, HPV 58, HPV 66, and HPV 69. In some embodiments, the HPV protein is HPV16 E5. In some embodiments, the subject has a cancer selected from the group consisting of: head and neck cancer, a mucosal squamous cell carcinoma, a cutaneous squamous cell carcinoma, cervical cancer, vaginal cancer, vulvar cancer, penile cancer, and anal cancer.

In some embodiments, the cancer is HPV-associated cancer. In some embodiments, the HPV-associated cancer is HPV-associated head and neck squamous cell carcinoma (HNSCC).

In some embodiments of any the methods described herein, an adamantane derivative, or pharmaceutically acceptable salt thereof, is administered in combination with a therapeutically effective amount of at least one additional therapeutic agent selected from one or more additional anti-cancer therapies or therapeutic (e.g., chemotherapeutic) agents. Using a combination of different forms of treatment to treat a subject with cancer is a common practice in medical oncology. These other form(s) of conjoint treatment or therapy, in addition to the adamantane derivatives described herein, can include, for example, surgery, radiotherapy, and additional anti-cancer agents, such as kinase inhibitors, signal transduction inhibitors, platinum-based chemotherapy, and/or monoclonal antibodies. In some embodiments, the method further comprises administering an additional anti-cancer agent.

Non-limiting examples of additional anti-cancer agents include: carboplatin, cisplatin, gemcitabine, methotrexate, paclitaxel, pemetrexed, lomustine, temozolomide, and dacarbazine.

In some embodiments, the additional anti-cancer agent is an immunotherapy. Many types of immunotherapies can be used in combination with the adamantane derivatives, or pharmaceutically acceptable salts thereof, described herein. Non-limiting examples of an immunotherapy include: immune checkpoint inhibitors, antibody therapy, cellular immunotherapy, antibody-drug conjugates, cytokine therapy, mRNA-based immunotherapy, and cancer vaccines.

In some embodiments, the immunotherapy is one or more immune checkpoint inhibitors. In some embodiments, the immune checkpoint inhibitor targets one or more of: CTLA-4, PD-1, PD-L1, BTLA, LAG-3, A2AR, TIM-3, B7-H3, VISTA, and IDO. In some embodiments, the checkpoint inhibitor is selected form the group consisting of: ipilimumab, nivolumab, pembrolizumab, atezolizumab, avelumab, durvalumab, cemiplimab-rwlc, tremelimumab, cemiplimab, and a combination thereof. In some embodiments, the immune checkpoint inhibitor is a CTLA-4 inhibitor, a PD-1 inhibitor or a PD-L1 inhibitor. In some embodiments, the CTLA-4 inhibitor is ipilimumab (YERVOY®) or tremelimumab (CP-675,206). In some embodiments, the PD-1 inhibitor is pembrolizumab (KEYTRUDA®), cemiplimab (LIBTAYO®), or nivolumab (OPDIVO®). In some embodiments, the PD-L1 inhibitor is atezolizumab (OPDIVO®), (TECENTRIQ®), avelumab (BAVENCIO®) or durvalumab (IMFINZI™).

In some embodiments, the antibody therapy is bevacizumab (MVASTI™, AVASTIN®), trastuzumab (HERCEPTIN®), avelumab (BAVENCIO®), rituximab (MABTHERA™, RITUXAN®), edrecolomab (Panorex), daratumuab (DARZALEX®), olaratumab (LARTRUVO™), ofatumumab (ARZERRA®), alemtuzumab (CAMPATH®), cetuximab (ERBITUX®), oregovomab, pembrolizumab (KEYTRUDA®), dinutiximab (UNITUXIN®), obinutuzumab (GAZYVA®), tremelimumab (CP-675,206), ramucirumab (CYRAMZA®), ublituximab (TG-1101), panitumumab (VECTIBIX®), elotuzumab (EMPLICITI™), avelumab (BAVENCIO®), necitumumab (PORTRAZZA™), cirmtuzumab (UC-961), ibritumomab (ZEVALIN®), isatuximab (SAR650984), nimotuzumab, fresolimumab (GC1008), lirilumab (INN), mogamulizumab (POTELIGEO®), ficlatuzumab (AV-299), denosumab (XGEVA®), ganitumab, urelumab, pidilizumab or amatuximab.

In some embodiments, the immunotherapy is a cellular immunotherapy (e.g., adoptive T-cell therapy, dendritic cell therapy, natural killer cell therapy).

In some embodiments, the immunotherapy is an antibody-drug conjugate. In some embodiments, the antibody-drug conjugate is gemtuzumab ozogamicin (MYLOTARG™), inotuzumab ozogamicin (BESPONSA®), brentuximab vedotin (ADCETRIS®), ado-trastuzumab emtansine (TDM-1; KADCYLA®), moxetumomab pasudotox (LUMOXITI®), polatuzumab vedotin-piiq (POLIVY®), mirvetuximab soravtansine (IMGN853), or anetumab ravtansine.

In some embodiments, the immunotherapy is a cytokine therapy. In some embodiments, the cytokine therapy is an interleukin 2 (IL-2) therapy, an interleukin 15 (IL-15) therapy, an interleukin 7 (IL-7) therapy, an interferon alpha (IFN$\alpha$) therapy, a granulocyte colony stimulating factor (G-CSF) therapy, an interleukin 12 (IL-12) therapy, or an erythropoietin-alpha (EPO) therapy. In some embodiments, the IL-2 therapy is aldesleukin (Proleukin®). In some embodiments, the IFNα therapy is interferon alfa-2b (e.g., IntronA®) or interferon alfa-2a (e.g., Roferon-A®). In some embodiments, the G-CSF therapy is filgrastim (Neupogen®).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26). See also, Pardi et al. Nat Rev Drug Discov. 2018 April; 17(4): 261-279, which is incorporated by reference herein in its entirety.

In some embodiments, the method comprises subjecting the subject to radiation therapy, surgery, or a combination thereof. For example, a surgery can be open surgery or minimally invasive surgery.

In some embodiments, the subject is refractory to standard therapy (e.g., standard of care). In some embodiments, the subject has no standard therapy option. In some embodiments, the subject relapsed or progressed after standard therapy. In some embodiments, the methods provided herein are useful for treating locally advanced or metastatic solid tumors refractory to standard therapies. For example, an HPV-associated cancer can be refractory to immune checkpoint inhibitors such as those described herein.

In some embodiments, the subject has a cancer that is refractory or intolerant to standard therapy (e.g., administration of a chemotherapeutic agent, an immunotherapy, or radiation). In some embodiments, the subject has a cancer (e.g., a locally advanced or metastatic tumor) that is refractory or intolerant to prior therapy (e.g., administration of a chemotherapeutic agent, immunotherapy (e.g., an immune checkpoint inhibitor), or radiation). In some embodiments, the cancer that is refractory or intolerant to standard therapy is an HPV-associated cancer. In some embodiments, the subject has a cancer (e.g., a locally advanced or metastatic tumor) that has no standard therapy.

In some embodiments, the subject has undergone prior therapy. In some embodiments, the subject received treatment with a platinum-based chemotherapy, immune checkpoint inhibitor (e.g., PD-1/PDL1 immunotherapy), radiation therapy, or a combination thereof, prior to treatment with an adamantane derivative, or pharmaceutically acceptable salt thereof.

Optimal dosages of an adamantane derivative, or pharmaceutically acceptable salt thereof, to be administered to a subject can be determined by those skilled in the art, and will vary with the mode of administration, the strength of the preparation, the mode of administration, and the advancement of the disease condition. In some embodiments, a subject can be administered a dosage of an adamantane derivative, or pharmaceutically acceptable salt thereof, of about 0.01 to 10,000 mg per adult human per day. For example, a pharmaceutical composition comprising an adamantane derivative, or pharmaceutically acceptable salt thereof, can be formulated to provide a dosage of about 0.01, about 0.05, about 0.1, about 0.5, about 1, about 2.5, about 5, about 10, about 15, about 25, about 50, about 100, about 150, about 200, about 250 or about 500 milligrams of the adamantane derivative, or pharmaceutically acceptable salt thereof. In some embodiments, an effective amount of an adamantane derivative, or pharmaceutically acceptable salt thereof, can be provided at a dosage level of about 0.1 mg/kg to about 1000 mg/kg of body weight per day, or any range therein. For example, about 0.5 to about 500 mg/kg of body weight per day, about 1.0 to about 250 mg/kg of body weight per day, about 0.1 to about 100 mg/kg of body weight per day, 0.1 to about 50.0 mg/kg of body weight per day, 15.0 mg/kg of body weight per day, or about 0.5 to about 7.5 mg/kg of body weight per day. An adamantane derivative, or pharmaceutically acceptable salt thereof, can be administered to a subject on a regimen of 1 to 4 times per day or in a single daily dose.

Pharmaceutical Compositions

Also provided herein are pharmaceutical compositions comprising an adamantane derivative, or pharmaceutically acceptable salt thereof, as described herein. Any of the pharmaceutical compositions described herein can be administered to a subject to treat a cancer as described herein.

Administration of the adamantane derivatives disclosed herein, or the pharmaceutically acceptable salts thereof, or pharmaceutical compositions thereof, can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Pharmaceutically acceptable compositions can include solid, semi-solid, liquid, solutions, colloidal, liposomes, emulsions, suspensions, complexes, coacervates and aerosols. Pharmaceutically acceptable compositions can also include dosage forms, such as, e.g., tablets, capsules, powders, liquids, suspensions, suppositories, aerosols, implants, controlled release or the like. The adamantane derivatives disclosed herein, or the pharmaceutically acceptable salts thereof, or pharmaceutical compositions thereof, can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate.

In some embodiments, the pharmaceutical composition is a tablet. In some embodiments, the pharmaceutical composition is a film-coated tablet.

The adamantane derivatives disclosed herein, or the pharmaceutically acceptable salts thereof, or pharmaceutical compositions thereof, can be administered either alone or in combination with a conventional pharmaceutical carrier, excipient or the like. Pharmaceutically acceptable excipients include, but are not limited to, ion exchangers, alumina, aluminum stearate, lecithin, self-emulsifying drug delivery systems (SEDDS) such as d-α-tocopherol, polyethylene glycol 1000, succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins can also be used to enhance delivery of compounds described herein.

In some embodiments, a pharmaceutical composition described herein will take the form of a unit dosage form such as a pill or tablet and thus the composition may contain, along with an adamantane derivative, or the pharmaceutically acceptable salt thereof, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more adamantane derivatives, or the pharmaceutically acceptable salts thereof, provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

In some embodiments, the pharmaceutical composition includes one or more excipients selected from the group consisting of: hypromellose, magnesium stearate, microcrystalline cellulose, and sodium starch glycolate.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

Dosage forms or compositions containing an adamantane derivatives as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22nd Edition (Pharmaceutical Press, London, UK. 2012).

The pharmaceutical compositions herein can contain, per unit dosage unit, e.g., tablet, capsule, suspension, solution, sachet for reconstitution, powder, injection, I.V., suppository, sublingual/buccal film, teaspoonful and the like, from about 0.1-1000 mg oof an adamantane derivative, or pharmaceutically acceptable salt thereof. The adamantane derivative, or pharmaceutically acceptable salt thereof, can be given at a dosage of from about 0.01-300 mg/kg/day, or any range therein, preferably from about 0.5-50 mg/kg/day, or any range therein. In some embodiments, the pharmaceutical compositions provided herein contain, per unit dosage unit, about 25 mg to about 500 mg of a compound provided herein (for example, about 25 mg to about 400 mg, about 25 mg to about 300 mg, about 25 mg to about 250 mg, about 25 mg to about 200 mg, about 25 mg to about 150 mg, about 25 mg to about 100 mg, about 25 mg to about 75 mg, about 50 mg to about 500 mg, about 100 mg to about 500 mg, about 150 mg to about 500 mg, about 200 mg to about 500 mg, about 250 mg to about 500 mg, about 300 mg to about 500 mg, about 400 mg to about 500 mg, about 50 to about 200 mg, about 100 to about 250 mg, about 50 to about 150 mg). In some embodiments, the pharmaceutical compositions provided herein contain, per unit dosage unit, about 25 mg, about 50 mg, about 100 mg, about 150 mg, about 200 mg, about 250 mg, about 300 mg, about 400 mg, or about 500 mg of a compound provided herein. The dosages, however, may be varied depending upon the requirement of the patients, the severity of the condition being treated and the compound being employed. In some embodiments, the dosages are administered once daily (QD) or twice daily (BID).

EXAMPLES

Example 1. Effect of Rimantidine and PEGylated Rimantidine in Mouse Cancer Models Methods Cell Lines AT-84-E7 and B16-OVA were grown in RPMI 1640 containing 10% FBS, 1% L-flutamine, 1% penicillin/streptomycin, 1% sodium pyruvate, and 200 μg/ml G418. DC2.4, RAW264.7, B3Z, 4T1, B16 and MC38 were grown in RPMI 1640 containing 10% FBS, 1% L-glutamine, 1% penicillin/streptomycin, and 1% sodium pyruvate. HEK293T was grown in DMEM containing 10% FBS, 1% L-glutamine, and 1% penicillin/streptomycin. 4MOSC1 was cultured in collagen-coated dish with K-SFM media (Invitrogen, Carlsbad, 20 CA) supplemented 1% penicillin/streptomycin, 5 ng/ml EGF (Invitrogen), and $2\times10^{-11}$ M cholera toxin (Sigma, St. Louis, MO) (27). CAL-27, CAL-33, and SCC-47 were grown in DMEM containing 10% FBS, 22 1% L-glutamine, and 1% penicillin/streptomycin. Routine monitoring for *Mycoplasma* contamination was performed using the MycoAlert PLUS Detection Kit (Lonza, Basel, Switzerland). All cell lines were used within ten passages after thawing.

Mouse Studies

Mice were injected subcutaneously with 1.0 to $5.0\times10^5$ AT-84-E7, $1.5\times10^5$ B16-OVA, or $5.0\times10^5$ 4T1 cells resuspended in 100 μl of PBS in the right flank. For orthotopic models, $1.0\times10^5$ AT-84-E7 or $1.0\times10^6$ 4MOSC1 in 30 μl of PBS were injected into tongue. Tumor diameter was measured every 2 to 3 days with an electronic caliper and reported as volume using the formula; tumor volume (mm3) =(length×width2)/2. Once tumors become palpable, mice were treated with 200 μg of anti-PD-L1 antibody (BioXcell, West Lebanon, NH) via IP injection every 3 days for a total of three or four injections per mouse, or mice were treated with 10 mg/kg body weight of rimantadine (Sigma, St. Louis, MO) via IP injection daily for 7 days. For adoptive transfer experiments, first, single-cell suspension of spleen from OT-1 mice were cultured in media containing 10 ng/ml OVA SIINFEKL peptide (InvivoGen, San Diego, CA) and 2 ng/ml recombinant IL-2 (PeproTech, Rocky Hill, NJ) for days, and then $4.0\times10^6$ cells were intravenously injected into B16-OVA-bearing mice.

Flow Cytometry

Single-cell suspensions were prepared from, lung, liver, tumor-draining lymph nodes, and tumors by mechanical dissociation and then filtered using a 70 μm filter. AT-84-E7 and MOC2 tumors were incubated in collagenase D (Roche, Basel, Switzerland) at 37° C. for 1 hour prior to mechanical dissociation. Density gradient centrifugation on 40%/80% Percoll (GE Healthcare, Chicago, IL) gradient was performed for single-cell suspension from tumors. After obtaining single-cell suspensions, each sample was incubated with an Fc blocking reagent (anti-CD16/32 antibody; BioLegend, San Diego, CA). Following Fc blockade, cells were stained with fluorescent-labeled antibodies [BioLegend, BD Bioscience (San Jose, CA), or eBiosciences (Thermo Fisher Scientific, Waltham, MA)]. LIVE/DEAD Fixable Cell Staining Kit (Invitrogen) was used for viability staining. For intracellular staining, cells were processed with Foxp3/Transcription Factor Fixation/Permeabilization Concentrate and Diluent (Invitrogen). Cells were analyzed using a BD FACS Aria II or LSR II flow cytometer (BD). Data was analyzed on FlowJo (FlowJo, LLC, Ashland, OR). For each antibody, the following clones were used: CD45.2 (104), CD3e (145-2C11), CD4 (RM4-5), CD8a (5H10), CD25 (3C7, PC61), CD44 (IM7), CD62L (MEL-14), IFN-γ (XMG1.2), Foxp3 (MF23), H-2Kb (AF6-88.5), H-2Kk (36-7-5), H-2Kd (SF1-1.1), H-2Kb/SIINFEKL (eBio25-D1.16), I-A/I-E (2G9), CD49b (DX5), CD11b (M1/70), FLAG (L5), CD31 (MEC13.3), NK-T/NK Cell Antigen (U5A2-13), CD102 (3C4 (MIC2/4)), CD62P (RMP-1), CD105 (MJ7/18), CD106 (429 (MVCAM.A)), and CD162 (2PH1). H-2Kb/SIINFEKL tetramer was purchased from MBL International (Woburn, MA).

Cell Cycle and Proliferation Assays

Cell cycle progression was analyzed on the basis of BrdU incorporation following 1 cell staining with BrdU-APC and 7-AAD using BD Pharmingen BrdU Flow Kit. (BD, Franklin Lakes, NJ) according to the manufacture's protocol. Cells were analyzed using flow cytometry. Cell proliferation was assessed by using MTT [3-(4,5-dimethylthiazol-2-yl)-2,5-diphenyltetrazolium bromide]. First, cells were seeded in 96-well plate and cultured for 2-3 days. Next, culture media was replaced with fresh media containing 0.5 mg/ml of MTT (Sigma) and the plates were incubated for 4 hours at 37° C. Then, purple formazan crystals were dissolved in lysis buffer (4 mM HCl and 0.1% NP-40 in isopropanol) and the absorbance was recorded on a TECAN infinite M200 microplate reader (Tecan, Männedorf, Switzerland) at a wavelength of 570 nm with absorbance at 650 nm as reference.

B3Z Activation Assay

B16-OVA cells were seeded into 96-well plate and treated with 100 μM rimantadine for 24 hours, prior to addition of B3Z cells. After 24 hours of co-culture, medium was removed and 100 μl of lysis buffer [0.155 mM chlorophenol red β-D-galactopyranoside (CPRG) (Roche), 0.125% Nonidet P-40 Alternative (EMD-Calbiochem), and 9 mM MgCl2 (Sigma) in PBS] was added. After incubation for 4 hours at 37° C., the absorbance at 570 nm was determined on a TECAN infinite M200 microplate reader.

Reverse Transcription and Quantitative PCR

Total RNA were extracted using TRIzol Reagent (Invitrogen) and reverse transcribed with qScript cDNA Synthesis Kit (Quanta BioSciences, Beverly, MA) according to the manufacturer's instructions. Quantitative PCR analysis were conducted by using KAPA SYBR 1 FAST (KAPA Biosystems, Wilmington, MA) on the 7900HT Fast Real-Time PCR System (Applied Biosystems, Foster City, CA).

Results

Figure 1A:
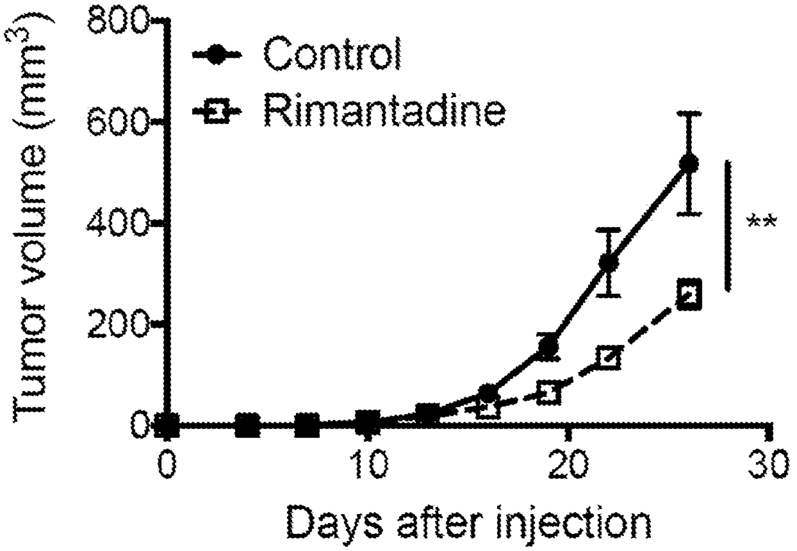
FIGS. 1A-1E are plots showing the effects of rimantadine or PEGylated rimantidine on tumor volume in different cancer models.
Figure 1B:
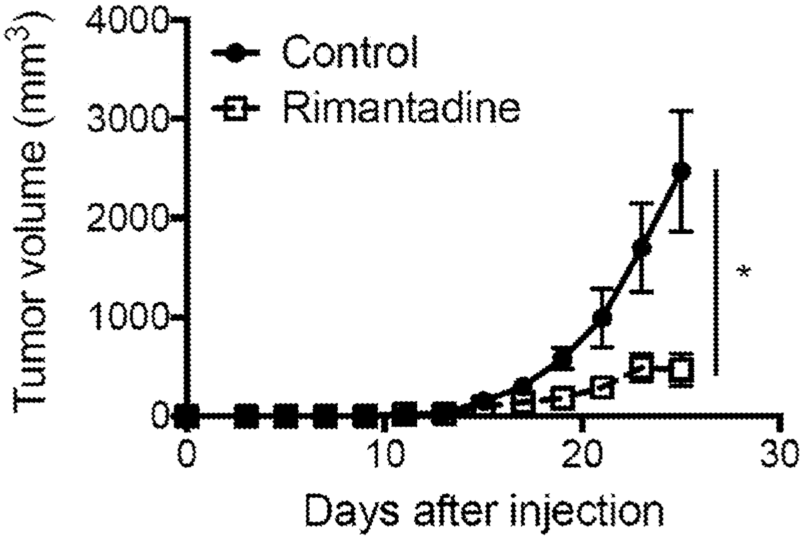
Figure 1C:
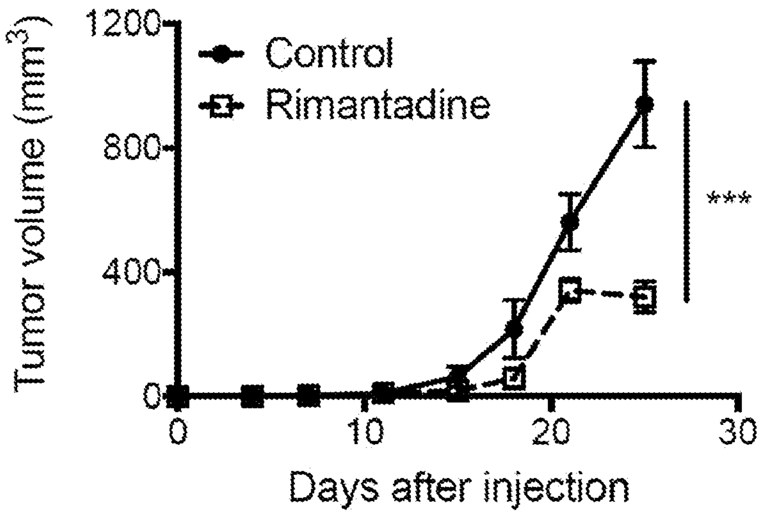
Figure 1D:
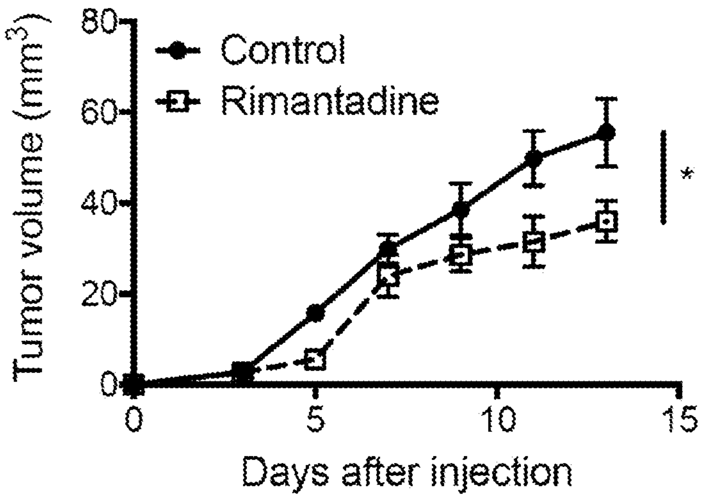
Figure 1E:
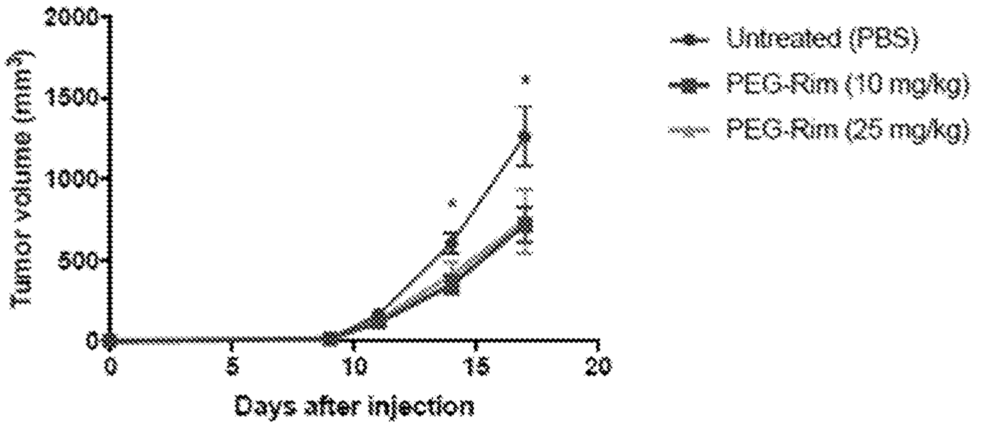
Figure 2A:
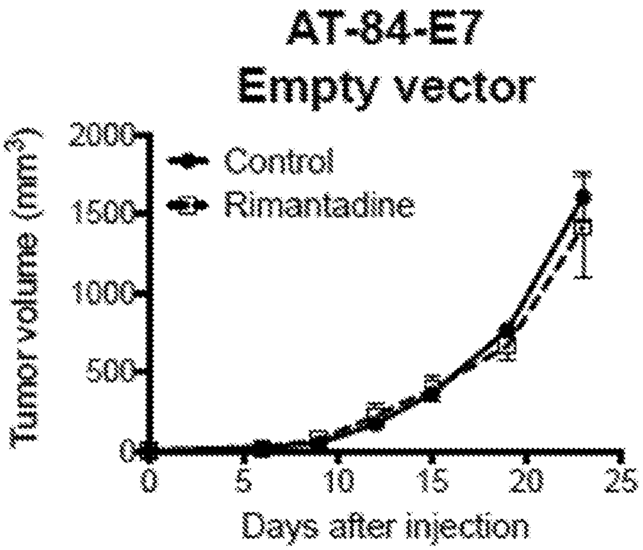
FIGS. 2A and 2B are plots showing the effects of rimantadine on tumor.
Figure 2B:
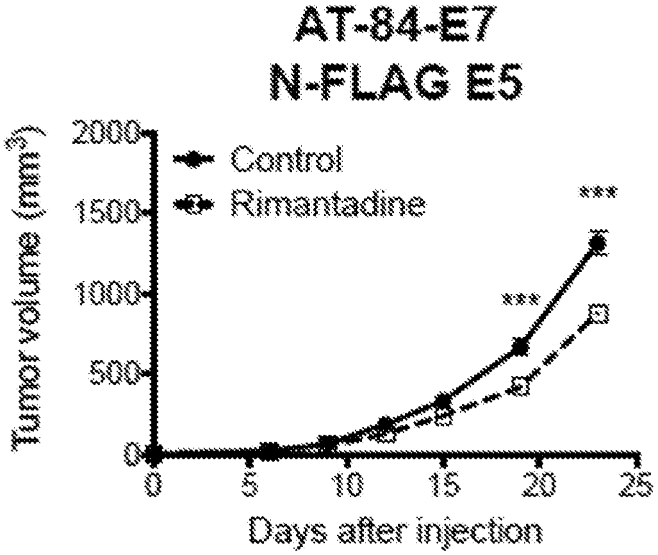

Rimantadine had anti-tumor activity alone and significantly decreased tumor growth (FIGS. 1A-1E). Rimantadine also had significant anti-tumor activity in 4MOSC1 HNSCC models as well as B16-OVA melanoma and 4T1 breast cancer models (FIGS. 1A-1D). Six mice were inoculated with $5\times10^5$ AT84-E7/E5 tumor cells and treated with intraperitoneal (IP) injections of 10 mg/kg body weight rimantadine once daily for a total of 7 injections starting on day 8. The tumor volumes were measured over the course of the experiment. Mice that received rimantadine had statistically significant decreases in tumor size compared to control groups as shown in FIG. 1A. Six mice were inoculated with $1.5\times10^5$ B16-OVA tumor cells and treated with IP injections of 10 mg/kg body weight rimantadine once daily for a total of 7 injections starting on day 10. The tumor volumes were measured over the course of the experiment. Mice that received rimantadine had statistically significant decreases in tumor sizes compared to control groups as shown in FIG. 1B. This experiment was repeated three times with similar results. Five mice were inoculated with $5\times10^5$ 4T1 tumor cells and treated with IP injections of 10 mg/kg body weight rimantadine once daily for a total of 7 injections starting on day 6. The tumor volumes were measured over the course of the experiment. Mice that received rimantadine had statistically significant decreases in tumor sizes compared to control groups as shown in FIG. 1C. Six mice were inoculated with $1.5\times10^5$ B16-OVA tumor cells and treated with IP injections of 10 mg/kg body weight PEGylated rimantadine (PEG-Rim) once daily for a total of 7 injections starting on day 10. The tumor volumes were measured over the course of the experiment. Mice that received PEGylated rimantadine had statistically significant decreases in tumor sizes compared to control groups as shown in FIG. 1E. The experiment was repeated twice with similar results. The anti-tumor effect of rimantadine were decreased in AT-84-E7 tumors which didn't express E5 (FIGS. 2A and 2B).

Significant increases in surface expression of MHC was observed in multiple cell lines (FIGS. 3A-3E and FIGS. 4A-D). Cell surface expression of MHC I on E5-positive AT-84-E7 was restored with rimantadine treatment (FIG. 3E).

To test the ability of rimantadine to enhance functional antigen presentation on tumor cells, B16 cells expressing OVA were used as a model tumor antigen and co-cultured with B3Z cells which respond to OVA SINNFKL peptide. Treatment of B16-OVA cells with rimantadine resulted in a significant 3-fold increase in recognition of this model tumor antigen by B3Z cells (FIG. 5). Rimantadine combined with anti-PD-L1 immunotherapy resulted in a significant improvement in survival in mice harboring B16-OVA tumors (FIG. 6).

The ability for rimantadine to increase expression of MHC on antigen presenting cells using the RAW264.7 cell line was tested and significant increases in both MHC class I and MHC class II surface expression were observed (FIGS. 7A and 7B). These findings demonstrate that rimantadine has anti-tumor activity in multiple pre-clinical tumor models and functions to enhance antigen presentation by upregulating MHC.

To study the direct cytotoxic activity of rimantadine, in vitro BrdU incorporation assays were performed to quantify the effects of rimantadine on cell cycling in human HNSCC cell lines. Rimantadine alone resulted in significant increases in GO/G1 cell cycle arrest and significant decreases in S phase in both AT-84-E7 and B16-OVA models (FIG. 8). Suppression of cell proliferation was also observed (FIG. 9). We also analyzed the effect of rimantadine on proliferation of T cells, but there was no significant effect (FIGS. 10A and 10B).

Changes in gene expression of cell cycle proteins were screened using RT-qPCR and significant decreases in microtubule and cell cycle regulatory molecule Stathmin after rimantadine treatment were identified (FIGS. 11A and B). Decreases in microtubule associated molecule Tau were also observed (FIGS. 12A and B).

To confirm rimantadine has activity against human head and neck tumor lines, BrdU incorporation assays and proliferation assays were performed. Significant cell cycle arrest and decreased proliferation with rimantadine alone were observed in the human CAL-27, CAL-33, and SCC-47 squamous cell carcinoma cell lines (FIG. 13). Finally, rimantadine induced cell cycle arrest in murine and human cell lines engineered to express HPV16 E5 (FIG. 14), indicating that rimantadine was able to functionally reverse effects of HPV E5.

Example 2. Effect of Rimantidine and PEGylated Rimantidine in Mouse Cancer Models Flow cytometry and MTT assays were performed as described in Example 1.

As shown in FIG. 15, rimantadine and memantine upregulated MHC Class I Expression in B16-OVA melanoma tumor line.

FIGS. 16A to 16C show that rimantadine and memantine inhibit proliferation of multiple murine head and neck cancer lines including B16-OVA melanoma, AT-84 E7 squamous cell carcinoma, and MOSCC3 squamous cell carcinoma. Additionally, rimantadine and memantine inhibited proliferation of human head and neck squamous cell carcinoma cell line CAL-27 at 48 and 72 hours (FIGS. 17A and 17B, respectively).

Other Embodiments

It is to be understood that while the invention has been described in conjunction with the detailed description thereof, the foregoing description is intended to illustrate and not limit the scope of the invention which is defined by the scope of the appended claims. Other aspects, advantages, and modification are within the scope of the following claims.

What is claimed is:

1. A method of treating a head and neck squamous cell carcinoma in a subject in need thereof, the method comprising administering to the subject a therapeutically effective amount of rimantadine, or a pharmaceutically acceptable salt thereof.

2. The method of claim 1, wherein the subject is administered a pharmaceutically acceptable salt of rimantadine.

3. The method of claim 2, wherein the pharmaceutically acceptable salt of rimantadine is a hydrochloride salt.

4. The method of claim 1, wherein cells of the head and neck squamous cell carcinoma express a human papilloma virus (HPV) protein.

5. The method of claim 4, wherein the HPV protein is one or more of an E5, E6, or E7 protein.

6. The method of claim 5, wherein the HPV E5, E6, or E7 protein is from one or more HPV subtypes selected from the group consisting of: HPV 6, HPV 11, HPV 16, HPV 18, HPV 31, HPV 33, HPV35, HPV 39, HPV 45, HPV51, HPV 52, HPV 56, HPV 48, HPV 66, and HPV 69.

7. The method of claim 6, wherein the HPV protein is HPV 16 E5.

8. The method of claim 1, wherein the head and neck squamous cell carcinoma is HPV-associated cancer.

9. A method of treating a head and neck squamous cell carcinoma in a subject, the method comprising:

contacting a cell of said head and neck squamous cell carcinoma in the subject, said cell comprising an HPV E5 protein, with a therapeutically effective amount of rimantadine, or a pharmaceutically acceptable salt thereof.

10. The method of claim 1, wherein the method further comprises administering at least one additional anti-cancer agent.

11. The method of claim 10, wherein the at least one additional anti-cancer agent is selected from the group consisting of: carboplatin, cisplatin, gemcitabine, methotrexate, paclitaxel, pemetrexed, lomustine, temozolomide, dacarbazine, and any combination thereof.

12. The method of claim 10, wherein the at least one additional anti-cancer agent is an immunotherapy agent.

13. The method of claim 10, wherein the at least one additional anti-cancer agent is an immune checkpoint inhibitor.

14. The method of claim 13, wherein the immune checkpoint inhibitor targets one or more of: CTLA-4, PD-1, PD-L1, BTLA, LAG-3, A2AR, TIM-3, B7-H3, VISTA, and IDO.

15. The method of claim 13, wherein the immune checkpoint inhibitor is selected from the group consisting of: ipilimumab, nivolumab, pembrolizumab, atezolizumab, avelumab, durvalumab, cemiplimab-rwlc, tremelimumab, cemiplimab, and any combination thereof.

16. The method of claim 1, wherein the method further comprises subjecting the subject to radiation therapy, surgery, or any combination thereof.

17. The method of claim 1, wherein the subject is a human.

* * * * *